(12) United States Patent
Xiong et al.

(10) Patent No.: US 12,176,491 B2
(45) Date of Patent: Dec. 24, 2024

(54) ELECTROLYTE AND ELECTROCHEMICAL APPARATUS USING SAME

(71) Applicant: Ningde Amperex Technology Limited, Ningde (CN)

(72) Inventors: Yali Xiong, Ningde (CN); Wenqiang Li, Ningde (CN); Mingming Guan, Ningde (CN); Jianming Zheng, Ningde (CN)

(73) Assignee: Ningde Amperex Technology Limited, Ningde (CN)

( * ) Notice: Subject to any disclaimer, the term of this patent is extended or adjusted under 35 U.S.C. 154(b) by 671 days.

(21) Appl. No.: 17/460,926

(22) Filed: Aug. 30, 2021

(65) Prior Publication Data
US 2022/0059873 A1    Feb. 24, 2022

Related U.S. Application Data

(63) Continuation of application No. PCT/CN2020/097491, filed on Jun. 22, 2020.

(51) Int. Cl.
| | |
|---|---|
| H01M 10/0569 | (2010.01) |
| C07C 255/04 | (2006.01) |
| C07C 255/05 | (2006.01) |
| C07C 255/16 | (2006.01) |
| C07C 309/06 | (2006.01) |
| C07D 207/46 | (2006.01) |
| C07D 327/10 | (2006.01) |
| H01M 10/0567 | (2010.01) |

(52) U.S. Cl.
CPC ....... *H01M 10/0569* (2013.01); *C07C 255/04* (2013.01); *C07C 255/05* (2013.01); *C07C 255/16* (2013.01); *C07C 309/06* (2013.01); *C07D 207/46* (2013.01); *C07D 327/10* (2013.01); *H01M 10/0567* (2013.01); *C07C 2601/14* (2017.05); *H01M 2300/0028* (2013.01)

(58) Field of Classification Search
CPC .......... H01M 10/0567; H01M 10/0569; C07D 207/46
See application file for complete search history.

(56) References Cited

U.S. PATENT DOCUMENTS

| | | | |
|---|---|---|---|
| 6,221,534 B1 | 4/2001 | Takeuchi et al. | |
| 7,223,502 B2 * | 5/2007 | Onuki | H01M 6/168 429/340 |
| 8,124,282 B2 | 2/2012 | Pan et al. | |
| 8,592,081 B2 * | 11/2013 | Utsumi | C07C 251/68 429/188 |
| 8,637,177 B2 * | 1/2014 | Nomura | H01G 9/02 429/144 |

(Continued)

FOREIGN PATENT DOCUMENTS

| | | | | |
|---|---|---|---|---|
| CN | 1877897 A | * | 12/2006 | .......... H01M 10/052 |
| CN | 102222798 A | | 10/2011 | |

(Continued)

OTHER PUBLICATIONS

Translation of written opinion (ETWOS) (no date) (Year: 0000).*
Machine translation of CN 109088099 (no date) (Year: 0000).*
Machine translation of JP 2007-200605 (no date) (Year: 0000).*
International Search Report and Written Opinion issued on Mar. 26, 2021 in corresponding International Application No. PCT/CN2020/097491; 10 pages.

(Continued)

*Primary Examiner* — Amanda C. Walke
(74) *Attorney, Agent, or Firm* — Maier & Maier, PLLC

(57) ABSTRACT

An electrolyte includes a compound of formula 1:

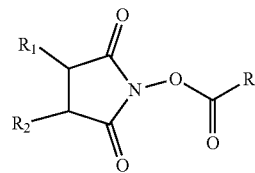

formula 1.

$R_1$ and $R_2$ are each independently selected from H, halogen atom, a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof. R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

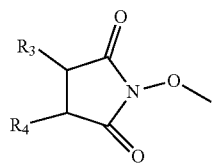

or any combination thereof.

20 Claims, No Drawings

(56) References Cited

U.S. PATENT DOCUMENTS

| | | | | |
|---|---|---|---|---|
| 9,923,238 | B2* | 3/2018 | Sawa | H01M 10/4235 |
| 11,031,626 | B2* | 6/2021 | Li | H01M 4/505 |
| 2007/0154815 | A1* | 7/2007 | Kawasaki | H01M 10/0436 |
| | | | | 429/231.95 |
| 2017/0125845 | A1* | 5/2017 | Yu | H01M 10/0568 |

FOREIGN PATENT DOCUMENTS

| | | | | | |
|---|---|---|---|---|---|
| CN | 103178291 | A | | 6/2013 | |
| CN | 105355968 | A | * | 2/2016 | H01M 10/0525 |
| CN | 106797051 | A | | 5/2017 | |
| CN | 107394267 | A | * | 11/2017 | H01M 10/0525 |
| CN | 107431248 | A | | 12/2017 | |
| CN | 105576282 | B | * | 11/2018 | H01M 10/052 |
| CN | 109088099 | A | * | 12/2018 | H01M 10/0525 |
| CN | 109860703 | A | | 6/2019 | |
| CN | 110336075 | A | | 10/2019 | |
| CN | 111628220 | A | * | 9/2020 | C07D 207/46 |
| JP | 2006344390 | A | * | 12/2006 | H01M 10/052 |
| JP | 2007200605 | A | | 8/2007 | |
| JP | 2020187973 | A | | 11/2020 | |
| WO | WO-0036675 | A1 | * | 6/2000 | H01M 4/13 |

OTHER PUBLICATIONS

Office Action issued on May 16, 2023, in corresponding Chinese Application No. 202080005813.3, 21 pages.

Office Action issued on Sep. 20, 2023, in corresponding Chinese Application No. 202080005813.3, 24 pages.

\* cited by examiner

ELECTROLYTE AND ELECTROCHEMICAL APPARATUS USING SAME

The present application is a continuation of International Application No. PCT/CN2020/097491, filed on 22 Jun. 2020, the disclosure of which is hereby incorporated by reference in its entirety.

TECHNICAL FIELD

This application relates to the technical field of electrochemical apparatuses, and in particular, to an electrolyte and an electrochemical apparatus using the same.

BACKGROUND

Along with the pursuit of batteries for small volume and high energy density, the increasing compacted density of positive and negative electrodes or the use of high-capacity negative electrode materials (such as lithium metal and Si/C negative electrodes) with poor cycle performance has caused a series of performance problems, such as poor cycle performance, poor high-temperature storage performance, and poor low-temperature performance and rate performance, and lithium plating easily occurs during low-temperature charging. How to solve such problems becomes a difficult problem hindering the development of secondary batteries.

SUMMARY

Embodiments of this application provide an electrolyte and an electrochemical apparatus using the same, in an attempt to solve at least one of the problems existing in the related art to some extent. The embodiments of this application further provide an electrochemical apparatus using the electrolyte and an electronic apparatus.

According to one aspect of this application provides an electrolyte, including a compound of formula 1:

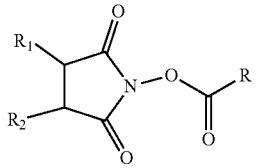

formula 1;

where $R_1$ and $R_2$ are each independently selected from H, halogen atom, a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof;

where R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

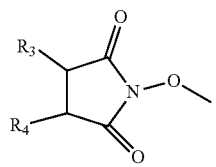

or any combination thereof;

where $R_3$ and $R_4$ are each independently selected from H, halogen, a substituted or unsubstituted $C_{1-3}$ alkyl group, a substituted or unsubstituted $C_{3-7}$ cycloalkyl group, a substituted or unsubstituted $C_{2-6}$ alkenyl group, a substituted or unsubstituted $C_{2-6}$ alkynyl group, a substituted or unsubstituted $C_{1-6}$ alkoxy group, or any combination thereof;

where when the substituent groups each are independently substituted, the substituent group is selected from at least one of halogen, a cyano group, a $C_{1-6}$ alkyl group, a $C_{3-6}$ cycloalkyl group, a $C_{1-6}$ alkoxy group, a $C_{2-6}$ alkenyl group, a $C_{6-10}$ aryl group, or a $C_{6-10}$ heteroaryl group; and where heteroatoms in the groups are each independently selected from at least one of O, S, N, or P.

According to some embodiments of this application, the compound of formula 1 includes at least one of the following compounds:

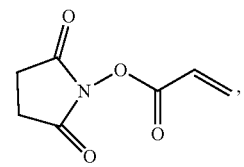

formula 1-1

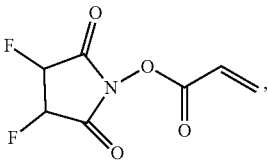

formula 1-2

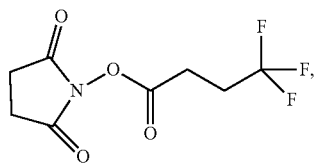

formula 1-3

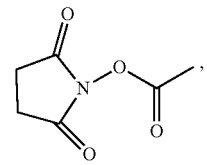

formula 1-4

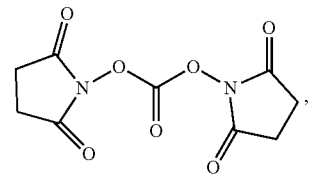

formula 1-5

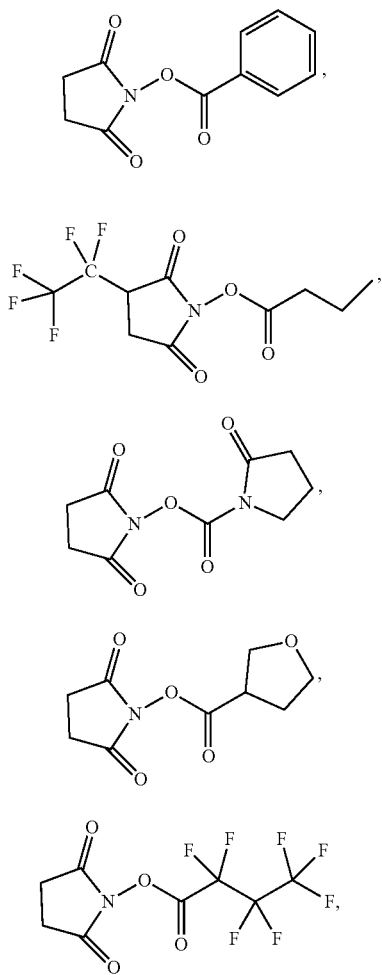

formula 1-6 formula 1-7 formula 1-8 formula 1-9 formula 1-10 formula 1-10, or

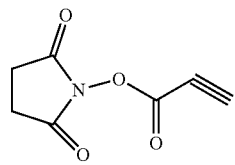

formula 1-11.

According to some embodiments of this application, based on a total weight of the electrolyte, the compound of formula 1 is 0.1 wt % to 10 wt %.

According to some embodiments of this application, the electrolyte further includes a nitrile compound, and the nitrile compound includes at least one of the compounds shown in formula 2, formula 3, formula 4 and formula 5:

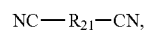 formula 2

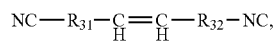 formula 3

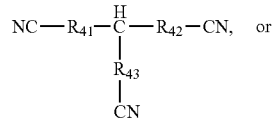 formula 4

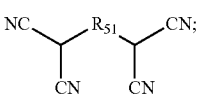 formula 5 where $R_{21}$ is selected from a substituted or unsubstituted $C_{1-5}$ alkylidene group or $R^c$—(O—$R^a$)$_A$—O—$R^b$, $R^a$ and $R^b$ are each independently selected from a substituted or unsubstituted $C_{1-3}$ alkylidene group, $R^c$ is selected from a single bonded or a substituted or unsubstituted $C_{1-3}$ alkylidene group, and A is an integer ranging from 0 to 2;

$R_{31}$ and $R_{32}$ are each independently selected from a single bonded or a substituted or unsubstituted $C_{1-5}$ alkylidene group;

$R_{41}$, $R_{42}$ and $R_{43}$ are each independently selected from a single bonded or a substituted or unsubstituted $C_{1-5}$ alkylidene group, a substituted or unsubstituted $C_{1-5}$ alkyleneoxy group, or any combination thereof;

where $R_{51}$ is selected from a substituted or unsubstituted $C_{1-5}$ alkylidene group, a substituted or unsubstituted $C_{3-7}$ cycloalkylidene group, a substituted or unsubstituted $C_{2-10}$ alkenylene group, a substituted or unsubstituted $C_{6-10}$ arylidene group, a substituted or unsubstituted $C_{1-6}$ heterocyclic group, or any combination thereof;

where when the substituent groups each are independently substituted, the substituent group is selected from at least one of halogen atom, a nitro group, a cyano group, a carboxyl group, and a sulfate group; and where based on the total weight of the electrolyte, the nitrile compound is 0.5 wt % to 10 wt %.

According to some embodiments of this application, the nitrile compound includes at least one of the following compounds:

 formula 2-1

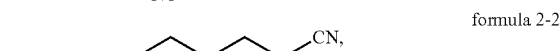 formula 2-2

 formula 2-3

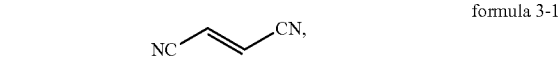 formula 3-1 formula 4-1

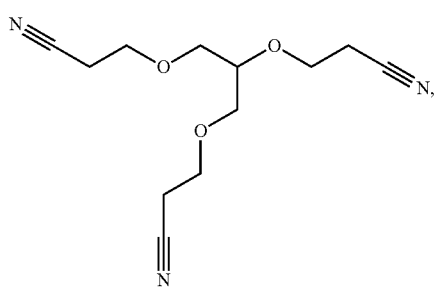

-continued

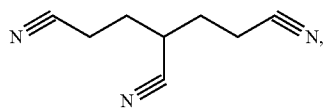
formula 4-2

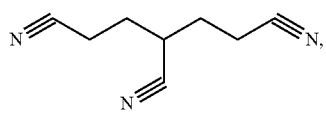
formula 4-3

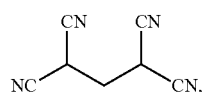
formula 5-1

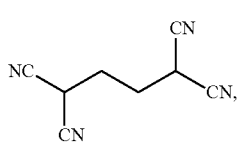
formula 5-2

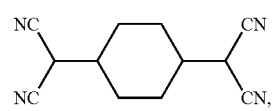
formula 5-3

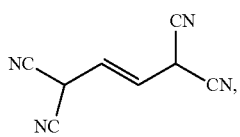
formula 5-4

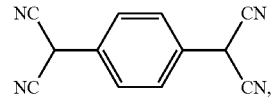
formula 5-5

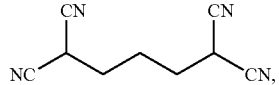
formula 5-6

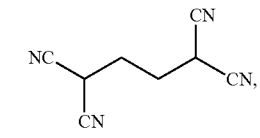
formula 5-7

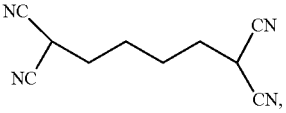
formula 5-8

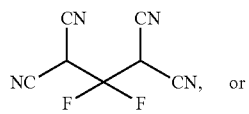
formula 5-9

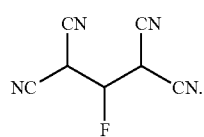
formula 5-10

According to some embodiments of this application, the electrolyte further includes a fluorosulfonic anhydride compound, and the fluorosulfonic anhydride compound includes a compound of formula 6:

formula 6

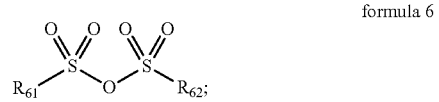

where $R_{61}$ and $R_{62}$ are each independently selected from a substituted or unsubstituted $C_{1-6}$ alkyl group, or $R_{61}$ and $R_{62}$ are combined with each other to generate a five- or six-membered ring; and where when the substituent groups are each independently substituted, the substituent group is selected from F atom.

In some embodiments, the fluorosulfonic anhydride compound includes at least one of the following compounds:

formula 6-1

formula 6-2

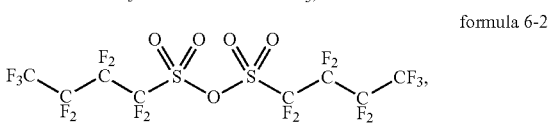

formula 6-3

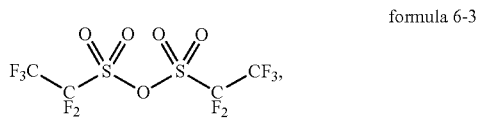

formula 6-4

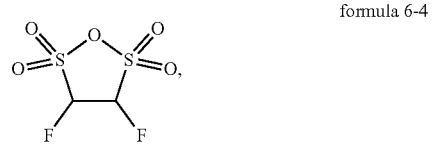

formula 6-5

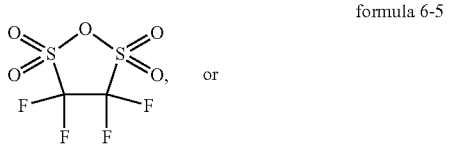

or formula 6-6

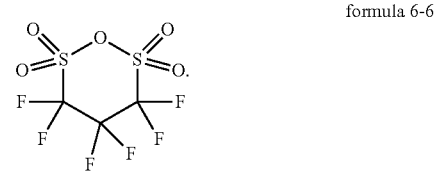

In another aspect of this application provides an electrochemical apparatus, including: a positive electrode, the positive electrode including a positive active material; a negative electrode, the negative electrode including a negative active material; and the electrolyte according to the embodiments of this application.

In some embodiments of this application, the positive active material of the electrochemical apparatus includes a lithium cobalt oxide, the lithium cobalt oxide includes an element M, and the element M is selected from one or more of Mg, Ti, Al, Zr, Sn, Zn, and Ca; and based on a total weight of the positive active material, the element M is 0.005 wt % to 1 wt %.

In some embodiments of this application, a specific surface area of the positive active material is 0.9 m$^2$/g to 1.5 m$^2$/g.

In another embodiment, this application provides an electronic apparatus, including the electrochemical apparatus according to the embodiments of this application.

According to the electrolyte of this application, a stable solid electrolyte interface (SEI) protective film is easily formed on the negative electrode in the chemical conversion process by introducing the compound of formula 1, to reduce side reaction of the electrolyte on the negative electrode, thereby improving the high-temperature cycle performance of a lithium-ion battery. Meanwhile, the nitrile compound and the fluorosulfonic anhydride compound with specific structures are added into the electrolyte, so that a compact and uniform SEI film with high lithium ion conductivity can be formed during first chemical conversion of the lithium-ion battery, the current distribution of the battery during charging and discharging is uniform, and the polarization is reduced, thereby improving the room-temperature cycle performance, high-temperature cycle performance, high-temperature storage performance and high-rate discharge performance of the lithium-ion battery.

Additional aspects and advantages of the embodiments of this application are partially described and presented in the later description, or explained by implementation of the embodiments of this application.

DESCRIPTION OF EMBODIMENTS

Embodiments of this application will be described in detail below. The embodiments of this application shall not be construed as a limitation on this application.

In the description of embodiments and claims, a list of items preceded by the terms such as "one of", "one type of" or other similar terms may mean any one of the listed items. For example, if items A and B are listed, the phrase "one of A and B" means only A or only B. In another example, if items A, B, and C are listed, the phrase "one of A, B, and C" means only A, only B, or only C. The item A may contain a single element or a plurality of elements. The item B may contain one element or a plurality of elements. The item C may contain one element or a plurality of elements.

In the description of embodiments and claims, a list of items preceded by the terms such as "at least one of", "at least one type of" or other similar terms may mean any combination of the listed items. For example, if items A and B are listed, the phrase "at least one of A and B" means only A, only B, or A and B. In another example, if items A, B, and C are listed, the phrase "at least one of A, B, and C" means only A, only B, only C, A and B (excluding C), A and C (excluding B), B and C (excluding A), or all of A, B, and C. The item A may contain a single element or a plurality of elements. The item B may contain one element or a plurality of elements. The item C may contain one element or a plurality of elements.

As used herein, the term "alkyl group" is intended to be a straight chain saturation alkane structure having 1 to 20 carbon atoms. The term "alkyl group" is also intended to be a branched or cyclic hydrocarbon structure having 3 to 20 carbon atoms. For example, an alkyl group may be an alkyl group having 1 to 20 carbon atoms, an alkyl group having 1 to 10 carbon atoms, an alkyl group having 1 to 5 carbon atoms, an alkyl group having 5 to 20 carbon atoms, an alkyl group having 5 to 15 carbon atoms, or an alkyl group having 5 to 10 carbon atoms. References to an alkyl group with a specific carbon number are intended to cover all geometric isomers with the specific carbon number. Therefore, for example, "butyl" is meant to include n-butyl, sec-butyl, isobutyl, tert-butyl, and cyclobutyl; and "propyl" includes n-propyl, isopropyl, and cyclopropyl. Examples of alkyl groups include, but are not limited to, methyl, ethyl, n-propyl, isopropyl, cyclopropyl, n-butyl, isobutyl, sec-butyl, tert-butyl, cyclobutyl, n-pentyl, isopentyl, neopentyl, cyclopentyl, methylcyclopentyl, ethylcyclopentyl, n-hexyl, isohexyl, cyclohexyl, n-heptyl, octyl, cyclopropyl, cyclobutyl, norbornyl, and the like. In addition, the alkyl group may be arbitrarily substituted.

As used herein, the term "cycloalkyl group" covers cyclic alkyl groups. A cycloalkyl group may be a cycloalkyl group having 3 to 20 carbon atoms, a cycloalkyl group having 6 to 20 carbon atoms, a cycloalkyl group having 3 to 12 carbon atoms, or a cycloalkyl group having 3 to 6 carbon atoms. For example, the cycloalkyl group may be a cyclopropyl group, a cyclobutyl group, a cyclopentyl group, a cyclohexyl group, and the like. In addition, the cycloalkyl group may be arbitrarily substituted.

As used herein, the term "cycloalkylene group" covers cyclic alkyl groups. A cycloalkylene group may be a cycloalkylene group having 3 to 20 carbon atoms, a cycloalkylene group having 6 to 20 carbon atoms, a cycloalkylene group having 3 to 12 carbon atoms, or a cycloalkylene group having 3 to 6 carbon atoms. For example, the cycloalkylene group may be a cyclopropylene group, a cyclobutylene group, a cyclopentylene group, a cyclohexylene group, and the like. In addition, the cycloalkylene group may be arbitrarily substituted.

As used herein, the term "heterocycloalkyl group" covers cyclic alkyl groups containing heteroatoms. A heterocycloalkyl group may be a heterocycloalkyl group having 3 to 20 carbon atoms, a heterocycloalkyl group having 6 to 20 carbon atoms, a heterocycloalkyl group having 3 to 12 carbon atoms, or a heterocycloalkyl group having 3 to 6 carbon atoms. For example, the heterocycloalkyl group may be a heterocyclopropyl group, a heterocyclobutyl group, a heterocyclopentyl group, a heterocyciohexyl group, and the like. In addition, the heterocycloalkyl group may be arbitrarily substituted.

As used herein, the term "alkoxy group" refers to an L-O— group, where L is an alkyl group. For example, an alkoxy group may be an alkoxy group having 1 to 20 carbon atoms, an alkoxy group having 1 to 12 carbon atoms, an alkoxy group having 1 to 5 carbon atoms, an alkoxy group having 5 to 20 carbon atoms, an alkoxy group having 5 to 15 carbon atoms, or an alkoxy group having 5 to 10 carbon atoms. In addition, the alkoxy group may be arbitrarily substituted.

As used herein, the term "alkyleneoxy group" refers to an -L$_1$-O— group, where L$_1$ is an alkylidene group. For example, an alkyleneoxy group may be an alkyleneoxy group having 1 to 20 carbon atoms, an alkyleneoxy group having 1 to 12 carbon atoms, an alkyleneoxy group having 1 to 5 carbon atoms, an alkyleneoxy group having 5 to 20 carbon atoms, an alkyleneoxy group having 5 to 15 carbon atoms, or an alkyleneoxy group having 5 to 10 carbon atoms. In addition, the alkyleneoxy group may be arbitrarily substituted.

As used herein, the term "alkenyl group" refers to a straight-chain or branched monovalent unsaturated hydrocarbon group having at least one and usually 1, 2, or 3 carbon-carbon double bonds. Unless otherwise defined, the alkenyl group generally contains 2 to 20 carbon atoms. For example, the alkenyl group may be an alkenyl group having 2 to 20 carbon atoms, an alkenyl group having 6 to 20 carbon atoms, an alkenyl group having 2 to 12 carbon atoms, or an alkenyl group having 2 to 6 carbon atoms. Representative alkenyl groups include, for example, vinyl, n-propenyl, isopropenyl, n-but-2-enyl, but-3-enyl, and n-hex-3-enyl. In addition, the alkenyl group may be arbitrarily substituted.

The term "alkynyl group" refers to a straight-chain or branched monovalent unsaturated hydrocarbon group having at least one and usually 1, 2, or 3 carbon-carbon triple bonds. Unless otherwise defined, the alkynyl group generally contains 2 to 20 carbon atoms. For example, the alkynyl group may be an alkynyl group having 2 to 20 carbon atoms, an alkynyl group having 6 to 20 carbon atoms, an alkynyl group having 2 to 10 carbon atoms, or an alkynyl group having 2 to 6 carbon atoms. Representative alkynyl groups include, for example, ethynyl, prop-2-ynyl (n-propynyl), n-but-2-ynyl, n-hex-3-ynyl, and the like. In addition, the alkynyl group may be arbitrarily substituted.

As used herein, the term "alkylidene group" means a straight-chain or branched chain divalent saturated hydrocarbon group. For example, an alkylidene group may be an alkylidene group having 1 to 20 carbon atoms, an alkylidene group having 1 to 15 carbon atoms, an alkylidene group having 1 to 10 carbon atoms, an alkylidene group having 1 to 5 carbon atoms, an alkylidene group having 5 to 20 carbon atoms, an alkylidene group having 5 to 15 carbon atoms, or an alkylidene group having 5 to 10 carbon atoms. Representative alkylidene groups include, for example, methylene, ethane-1,2-diyl ("ethylene"), propane-1,2-diyl, propane-1,3-diyl, butane-1,4-diyl, and pentane-1,5-diyl, and the like. In addition, the alkylidene group may be arbitrarily substituted.

As used herein, the term "alkenylene group" covers straight-chain and branched chain alkenylene groups. References to an alkenylene group with a specific carbon number are intended to cover all geometric isomers with the specific carbon number. For example, an alkenylene group may be an alkenylene group having 2 to 20 carbon atoms, an alkenylene group having 2 to 15 carbon atoms, an alkenylene group having 2 to 10 carbon atoms, an alkenylene group having 2 to 5 carbon atoms, an alkenylene group having 5 to 20 carbon atoms, an alkenylene group having 5 to 15 carbon atoms, or an alkenylene group having 5 to 10 carbon atoms. Representative alkenylene groups include, for example, vinylene, propenylene, and butenylene. In addition, the alkenylene group may be arbitrarily substituted.

As used herein, the term "aryl group" covers monocyclic and polycyclic systems. Polycycles may have two or more rings in which two carbons are shared by two adjoining rings (the rings are "fused"), at least one of the rings is aromatic, for example, the other rings may be cycloalkyl groups, cycloalkenyl groups, aryl groups, heterocycles and/or heteroaryl groups. For example, an aryl group may be a $C_6$-$C_{50}$ aryl group, a $C_6$-$C_{40}$ aryl group, a $C_6$-$C_{30}$ aryl group, a $C_6$-$C_{20}$ aryl group, or a $C_6$-$C_{10}$ aryl group. Representative aryl groups include, for example, phenyl, methylphenyl, propylphenyl, isopropylphenyl, benzyl, naphth-1-yl, naphth-2-yl, and the like. In addition, the aryl group may be arbitrarily substituted.

As used herein, the term "arylidene group" covers $C_6$-$C_{50}$ arylidene groups, $C_6$-$C_{40}$ arylidene groups, $C_6$-$C_{30}$ arylidene groups, $C_6$-$C_{20}$ arylidene groups, or $C_6$-$C_{10}$ arylidene groups. Representative arylidene groups include, for example, phenylene, methylenephenyl, propylenephenyl, isopropylenephenyl, benzylen, and the like. In addition, the arylidene group may be arbitrarily substituted.

As used herein, the term "heteroaryl group" covers monocyclic heteroaromatic groups which may include one to three heteroatoms, such as pyrrole, furan, thiophene, imidazole, oxazole, thiazole, triazole, pyrazole, pyridine, pyrazine and pyrimidine. The term "heteroaryl group" also includes polycyclic heteroaromatic systems having two or more rings in which two atoms are shared by two adjoining rings (the rings are "fused"), at least one of the rings is a heteroaryl group, and the other rings may be cycloalkyl groups, cycloalkenyl groups, aryl groups, heterocycles and/or heteroaryl groups. Heteroatoms in the heteroaryl group may be, for example, O, S, N, Se, and the like. For example, a heteroaryl group may be a $C_3$-$C_{50}$ heteroaryl group, a $C_3$-$C_{40}$ heteroaryl group, a $C_3$-$C_{30}$ heteroaryl group, a $C_3$-$C_{20}$ heteroaryl group, or a $C_3$-$C_{10}$ heteroaryl group. In addition, the heteroaryl group may be arbitrarily substituted.

As used herein, the term "heterocyclic group" covers aromatic and non-aromatic cyclic groups. Heteroaromatic cyclic groups also mean heteroaryl groups. In some embodiments, a heterocyclic group is a $C_1$-$C_{50}$ heterocyclic group, a $C_1$-$C_{40}$ heterocyclic group, a $C_1$-$C_{30}$ heterocyclic group, a $C_1$-$C_{20}$ heterocyclic group, a $C_1$-$C_{10}$ heterocyclic group, or a $C_1$-$C_6$ heterocyclic group including at least one heteroatom. For example, the heterocyclic groups include morpholinyl, piperidinyl, pyrrolidinyl, and cyclic ethers such as tetrahydrofuran and tetrahydropyran. In addition, the heterocyclic group may be arbitrarily substituted.

As used herein, the term "heteroatom" covers O, S, P, N, B, or an isostere thereof.

As used herein, the term "halogen" covers F, Cl, Br, and I.

When the substituent groups are substituted, their substituent groups each may independently be selected from the group consisting of: halogen, an alkyl group, an alkenyl group, and an aryl group. As used herein, the term "substitute" or "substituted" means substitution by 1 or more (for example, 2 or 3) substituent groups.

As used herein, the content of each component is obtained based on the total weight of the electrolyte.

I. Electrolyte

In some embodiments, this application provides an electrolyte, including a compound of formula 1:

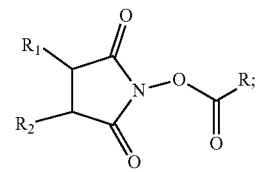

formula 1 where $R_1$ and $R_2$ are each independently selected from H, halogen atom, a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof;

where R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

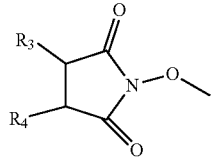

or any combination thereof;

where $R_3$ and $R_4$ are each independently selected from H, halogen atom, a substituted or unsubstituted $C_{1-3}$ alkyl group, a substituted or unsubstituted $C_{3-7}$ cycloalkyl group, a substituted or unsubstituted $C_{2-6}$ alkenyl group, a substituted or unsubstituted $C_{2-6}$ alkynyl group, a substituted or unsubstituted $C_{1-6}$ alkoxy group, or any combination thereof;

where when the substituent groups are each independently substituted, the substituent group is selected from at least one of halogen, a cyano group, a $C_{1-6}$ alkyl group, a $C_{3-6}$ cycloalkyl group, a $C_{1-6}$ alkoxy group, a $C_{2-6}$ alkenyl group, a $C_{6-10}$ aryl group, or a $C_{6-10}$ heteroaryl group; and where heteroatoms in the groups each are independently selected from at least one of O, S, N, or P.

In some embodiments, $R_1$ and $R_2$ each are independently selected from H, halogen atom, a substituted or unsubstituted $C_{1-10}$ alkyl group, or any combination thereof;

where R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

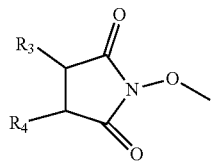

or any combination thereof; and where $R_3$ and $R_4$ are each independently selected from H or halogen atom.

In some embodiments, $R_1$ and $R_2$ are each independently selected from H, halogen atom, a substituted or unsubstituted $C_{1-5}$ alkyl group, or any combination thereof;

where R is selected from a substituted or unsubstituted $C_{1-5}$ alkyl group, a substituted or unsubstituted $C_{3-5}$ cycloalkyl group, a substituted or unsubstituted $C_{2-5}$ alkenyl group, a substituted or unsubstituted $C_{2-5}$ alkynyl group, a substituted or unsubstituted $C_{1-5}$ alkoxy group, a substituted or unsubstituted $C_{6-8}$ aryl group or a substituted or unsubstituted $C_{3-5}$ heteroaryl group, a substituted or unsubstituted $C_{3-5}$ heterocycloalkyl group, a butyrolactam group,

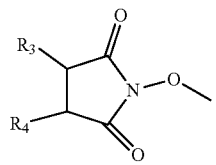

or any combination thereof; and where $R_3$ and $R_4$ are each independently selected from H or halogen atom.

In some embodiments, the compound of formula 1 in the electrolyte includes at least one of the following compounds:

formula 1-1

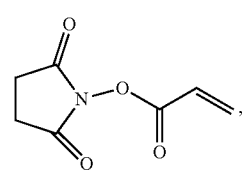

formula 1-2

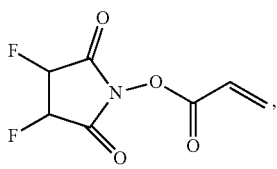

formula 1-3

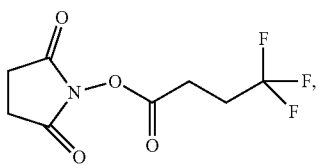

formula 1-4

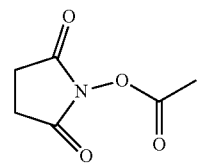

formula 1-5

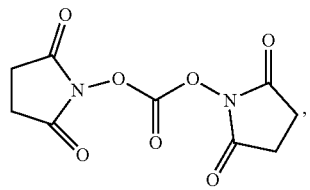

formula 1-6

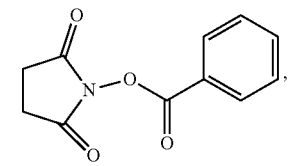

formula 1-7

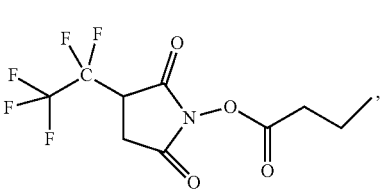

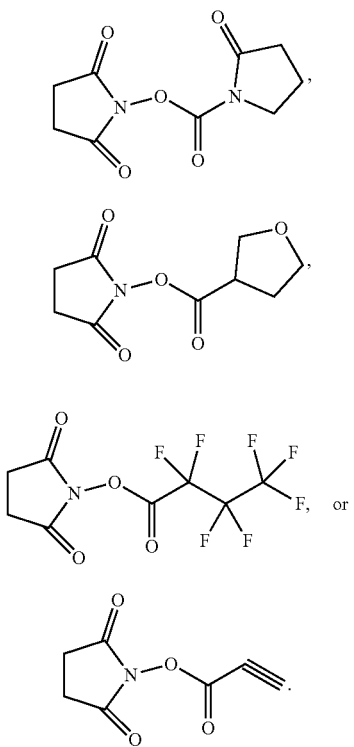

formula 1-8 formula 1-9 formula 1-10 formula 1-11

In some embodiments, based on a total weight of the electrolyte, the compound of formula 1 is 0.1 wt % to 10 wt %. In some embodiments, based on the total weight of the electrolyte, the weight percentage of the compound of formula 1 is 0.1 wt %, 0.3 wt %, 0.5 wt %, 1 wt %, 1.5 wt %, 2 wt %, 2.5 wt %, 3 wt %, 3.5 wt %, 4 wt %, 4.5 wt %, 5 wt %, 6 wt %, 7 wt %, 8 wt %, 9 wt %, or 10 wt %, or in a range defined by any two of these values.

In some embodiments of this application, the electrolyte further includes a nitrile compound, and the nitrile compound includes at least one of the compounds shown in formula 2, formula 3, formula 4 and formula 5:

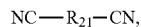

formula 2

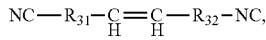

formula 3

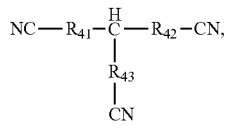

formula 4

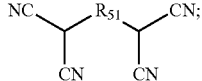

formula 5 where $R_{21}$ is selected from a substituted or unsubstituted $C_{1-5}$ alkylidene group or $R^c$—$(O$—$R^a)_A$—$O$—$R^b$, $R^a$ and $R^b$ each are independently selected from a substituted or unsubstituted $C_{1-3}$ alkylidene group, $R^c$ is selected from a single bonded or a substituted or unsubstituted $C_{1-3}$ alkylidene group, and A is an integer ranging from 0 to 2;

$R_{31}$ and $R_{32}$ are each independently selected from a single bonded or a substituted or unsubstituted $C_{1-5}$ alkylidene group;

$R_{11}$, $R_{42}$ and $R_{43}$ are each independently selected from a single bonded or a substituted or unsubstituted $C_{1-5}$ alkylidene group, or a substituted or unsubstituted $C_{1-5}$ alkyleneoxy group;

where $R_{51}$ is selected from a substituted or unsubstituted $C_{1-5}$ alkylidene group, a substituted or unsubstituted $C_{3-7}$ cycloalkylidene group, a substituted or unsubstituted $C_{2-10}$ alkenylene group, a substituted or unsubstituted $C_{6-10}$ arylene group, a substituted or unsubstituted $C_{1-6}$ heterocyclic group, or any combination thereof; and where when the substituent groups are each independently substituted, the substituent group is selected from at least one of halogen, a nitro group, a cyano group, a carboxyl group, and a sulfate group.

In some embodiments, the nitrile compound includes at least one of the following compounds:

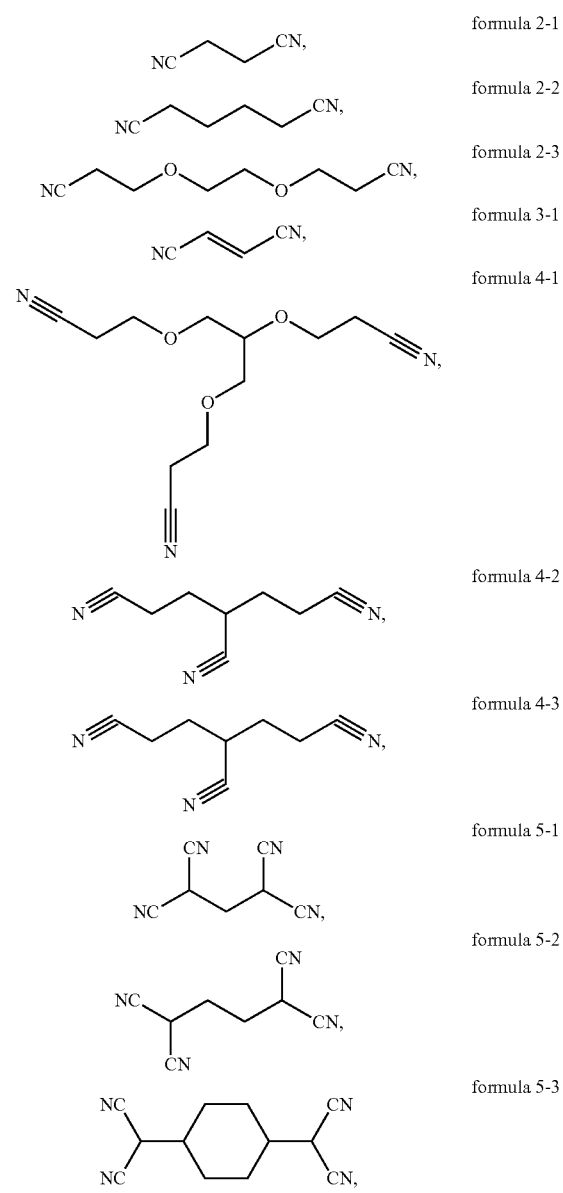

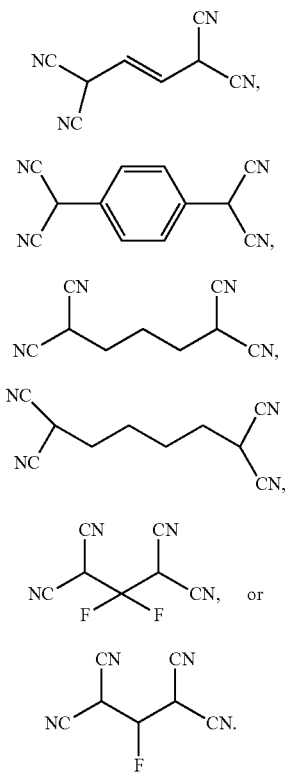

In some embodiments, based on the total weight of the electrolyte, the nitrile compound is 0.5 wt % to 10 wt %. In some embodiments, based on the total weight of the electrolyte, the nitrile compound is 0.5 wt %, 1 wt %, 1.5 wt %, 2 wt %, 2.5 wt %, 3 wt %, 3.5 wt %, 4 wt %, 4.5 wt %, 5 wt %, 6 wt %, 7 wt %, 8 wt %, 9 wt %, or 10 wt %, or in a range defined by any two of these values.

In some embodiments, the electrolyte further includes a fluorosulfonic anhydride compound, and the fluorosulfonic anhydride compound includes a compound of formula 6:

formula 6

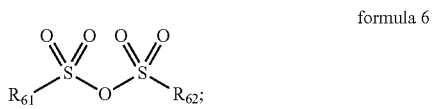

where $R_{61}$ and $R_{62}$ are each independently selected from a substituted or unsubstituted $C_{1-6}$ alkyl group, or $R_{61}$ and $R_{62}$ are combined with each other to generate a five- or six-membered ring; and where when the substituent groups are each independently substituted, the substituent group is selected from F.

In some embodiments, the fluorosulfonic anhydride compound includes at least one of the following compounds:

formula 6-1

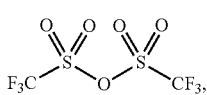

formula 6-2

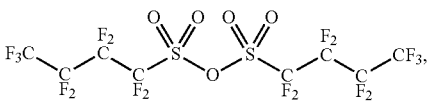

formula 6-3

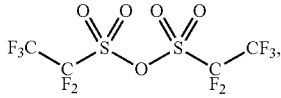

formula 6-4

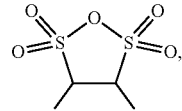

formula 6-5

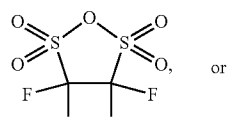

or formula 6-6

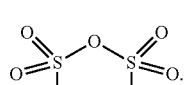

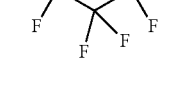

In some embodiments, based on the total weight of the electrolyte, the fluorosulfonic anhydride compound is 0.1 wt % to 5 wt %. In some embodiments, based on the total weight of the electrolyte, the fluorosulfonic anhydride compound is 0.1 wt %, 0.3 wt %, 0.5 wt %, 1.0 wt %, 1.5 wt %, 2.0 wt %, 2.5 wt %, 3 wt %, 3.5 wt %, 4 wt %, 4.5 wt %, or 5 wt %, or in a range defined by any two of these values.

In some embodiments, the electrolyte further includes a cyclic ether. The cyclic ether can simultaneously form a film on a positive electrode and a negative electrode, thereby reducing the reaction of the electrolyte with active materials.

In some embodiments, the cyclic ether includes, but is not limited to: at least one of tetrahydrofuran, 2-methyl tetrahydrofuran, 1,3-dioxolane, 2-methyl 1,3-dioxolane, 4-methyl 1,3-dioxolane, 1,3-dioxane, 1,4-dioxane, or dimethoxypropane.

In some embodiments, based on the total weight of the electrolyte, a weight percentage of the cyclic ether is 0.1 wt % to 10 wt %. In some embodiments, based on the total weight of the electrolyte, the weight percentage of the cyclic ether is not less than 0.1 wt %. In some embodiments, based on the total weight of the electrolyte, the weight percentage of the cyclic ether is not less than 0.5 wt %. In some embodiments, based on the total weight of the electrolyte, the weight percentage of the cyclic ether is not more than 2 wt %. In some embodiments, based on the total weight of the electrolyte, the weight percentage of the cyclic ether isless than or equal to 5 wt %.

In some embodiments, the electrolyte further includes a chain ether. In some embodiments, the chain ether includes, but is not limited to: at least one of dimethoxymethane, 1,1-dimethoxyethane, 1,2-dimethoxyethane, diethoxymethane, 1,1-diethoxy ethane, 1,2-diethoxy ethane, ethoxymethoxyethane, 1,1-ethoxymethoxyethane, or 1,2-ethoxymethoxyethane.

In some embodiments, based on the total weight of the electrolyte, the chain ether is 0.1 wt % to 10 wt %. In some embodiments, based on the total weight of the electrolyte, the chain ether is more than or equal to 0.5 wt %. In some embodiments, based on the total weight of the electrolyte, the chain ether ismore than or equal to 2 wt %. In some embodiments, based on the total weight of the electrolyte, the chain ether is more than or equal to 3 wt %. In some embodiments, based on the total weight of the electrolyte, the chain ether is less than or equal to 10 wt %. In some embodiments, based on the total weight of the electrolyte, the chain ether is less than or equal to 5 wt %.

In some embodiments, the electrolyte further includes an aromatic fluorine-containing solvent. The aromatic fluorine-containing solvent can form a film fast to protect the active materials, and the fluorine-containing substance can improve the infiltration performance of the electrolyte to the active materials. In some embodiments, the aromatic fluorine-containing solvent includes, but is not limited to: at least one of fluorobenzene, difluorobenzene, trifluorobenzene, tetrafluorobenzene, pentafluorobenzene, hexafluorobenzene, or benzotrifluoride.

In some embodiments, based on the total weight of the electrolyte, the aromatic fluorine-containing solvent is about 0.1 wt % to 10 wt %. In some embodiments, based on the total weight of the electrolyte, t the aromatic fluorine-containing solvent is more than or equal to 0.5 wt %. In some embodiments, based on the total weight of the electrolyte, the aromatic fluorine-containing solvent is more than or equal to 2 wt %. In some embodiments, based on the total weight of the electrolyte, the weight percentage of the aromatic fluorine-containing solvent is less than or equal to 4 wt %. In some embodiments, based on the total weight of the electrolyte, the aromatic fluorine-containing solvent is less than or equal to 8 wt %.

In some embodiments, the electrolyte further includes a lithium salt additive. In some embodiments, the lithium salt additive includes, but is not limited to, at least one of lithium trifluoromethane sulfonimide $LiN(CF_3SO_2)_2$ (LiTFSI for short), lithium bis(fluorosulfonyl)imide $Li(N(SO_2F)_2)$ (LiFSI for short), lithium bisoxalate borate $LiB(C_2O_4)_2$ (LiBOB for short), lithium tetrafluorophosphate oxalate $(LiPF_4C_2O_2)$, lithium difluorooxalato borate $LiBF_2(C_2O_4)$ (LiDFOB for short), or lithium hexafluorocesiumate $(LiCsF_6)$.

In some embodiments, based on the total weight of the electrolyte, the lithium salt additive is 0.01 wt % to 10 wt %. In some embodiments, based on the total weight of the electrolyte, the lithium salt additive is 0.1 wt % to 5 wt %. In some embodiments, based on the total weight of the electrolyte, the lithium salt additive is 0.1 wt %, 1 wt %, 3 wt %, 5 wt %, 7 wt %, 9 wt %, or 10 wt %, or in a range defined by any two of these values.

II. Electrolyte

An electrolyte used in the electrolyte of the embodiments of this application may be an electrolyte known in the art. The electrolyte includes, but is not limited to: an inorganic lithium salt, such as $LiClO_4$, $LiAsF_6$, $LiPF_6$, $LiBF_4$, $LiSbF_6$, $LiSO_3F$, and $LiN(FSO_2)_2$; a fluorine-containing organic lithium salt, such as $LiCF_3SO_3$, $LiN(FSO_2)(CF_3SO_2)$, $LiN(CF_3SO_2)_2$, $LiN(C_2F_5SO_2)_2$, cyclic lithium 1,3-hexafluoropropane disulfonimide, cyclic lithium 1,2-tetrafluoroethane disulfonimide, $LiN(CF_3SO_2)(C_4F_9SO_2)$, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_2(CF_3)_2$, $LiBF_2(C_2F_5)_2$, $LiBF_2(CF_3SO_2)_2$, and $LiBF_2(C_2F_5SO_2)_2$; and a lithium salt containing a dicarboxylic acid complex, such as lithium bis(oxalato)borate, lithium difluorooxalatoborate, lithium tris(oxalato)phosphate, lithium difluorobis(oxalato)phosphate, and lithium tetrafluoro(oxalato)phosphate. In addition, one electrolyte may be used alone, or two or more electrolytes may be used simultaneously. For example, in some embodiments, the electrolyte includes a combination of $LiPF_6$ and $LiBF_4$. In some embodiments, the electrolyte includes a combination of an inorganic lithium salt such as $LiPF_6$ or $LiBF_4$ and a fluorine-containing organic lithium salt such as $LiCF_3SO_3$, $LiN(CF_3SO_2)_2$ or $LiN(C_2F_5SO_2)_2$. In some embodiments, the concentration of the electrolyte is in the range of 0.8 to 3 mol/L, for example, in the range of 0.8 to 2.5 mol/L, in the range of 0.8 to 2 mol/L, in the range of 1 to 2 mol/L, in the range of 0.5 to 1.5 mol/L, in the range of 0.8 to 1.3 mol/L, or in the range of 0.5 to 1.2 mol/L, and for example, is 1 mol/L, 1.15 mol/L, 1.2 mol/L, 1.5 mol/L, 2 mol/L, or 2.5 mol/L.

III. Electrochemical Apparatus

The electrochemical apparatus according to this application includes any apparatus in which an electrochemical reaction takes place. Specific examples of the apparatus include all kinds of primary batteries, secondary batteries, fuel batteries, solar batteries, or capacitors. Especially, the electrochemical apparatus is a lithium secondary battery, including a lithium metal secondary battery, a lithium-ion secondary battery, a lithium polymer secondary battery, or a lithium-ion polymer secondary battery. In some embodiments, the electrochemical apparatus according to this application is an electrochemical apparatus provided with a positive electrode having a positive active material capable of occluding and releasing metal ions, and a negative electrode having a negative active material capable of occluding and releasing metal ions. The electrochemical apparatus includes the electrolyte in any one of the foregoing embodiments of this application.

1. Electrolyte

An electrolyte used in the electrochemical apparatus according to this application is the electrolyte in any one of the foregoing embodiments of this application.

In addition, the electrolyte used in the electrochemical apparatus according to this application may also include other electrolytes within the scope not departing from the essence of this application.

2. Negative Electrode

The material, composition and manufacturing method of a negative electrode used in the electrochemical apparatus according to this application may include any technology disclosed in the prior art. In some embodiments, the negative electrode is the negative electrode described in U.S. patent application U.S. Pat. No. 9,812,739B, which is incorporated herein by reference in its entirety.

In some embodiments, the negative electrode includes a electrode current collector and a negative active material layer on the current collector. The negative active material includes a material that reversibly intercalates and deintercalates lithium ions. In some embodiments, the material that reversibly intercalates and deintercalates lithium ions includes a carbon material. In some embodiments, the carbon material may be any carbon-based negative active material commonly used in a lithium-ion rechargeable battery. In some embodiments, the carbon material includes, but is not limited to: crystalline carbon, amorphous carbon, or a mixture thereof. The crystalline carbon may be amorphous, plate-shaped, flake-shaped, spherical or fiber-shaped natural graphite or artificial graphite. The amorphous carbon may be soft carbon, hard carbon, a mesophase pitch carbide, calcined coke, or the like.

In some embodiments, the negative active material layer includes a negative active material. In some embodiments, the negative active material includes, but is not limited to: lithium metal, structured lithium metal, natural graphite, artificial graphite, mesocarbon microbeads (MCMB), hard carbon, soft carbon, silicon, a silicon-carbon compound, a Li—Sn alloy, a Li—Sn— alloy, Sn, SnO, $SnO_2$, spinel-structure lithiated $TiO_2$-$Li_4Ti_5O_{12}$, a Li—Al alloy, or any combination thereof.

When the negative electrode includes a silicon-carbon compound, the ratio of silicon to carbon is 1:10 to 10:1 based on a total weight of the negative active material, and a median particle diameter Dv50 of the silicon-carbon compound is 0.1 µm to 100 µm. When the negative electrode includes an alloy material, the negative active material layer may be formed by an evaporation method, a sputtering method, a plating method, or the like. When the negative electrode includes lithium metal, for example, the negative active material layer is formed from a spherical stranded conductive skeleton and metal particles dispersed in the conductive skeleton. In some embodiments, the spherical stranded conductive skeleton may have a porosity of 5% to 85%. In some embodiments, a protective layer may also be provided on the lithium metal negative active material layer.

In some embodiments, the negative active material layer may include a binder, and optionally includes a conductive material. The binder enhances binding between particles of the negative active material, and binding between the negative active material and the current collector. In some embodiments, the binder includes, but is not limited to: polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(vinylidene fluoride), polyethylene, polypropylene, styrene-butadiene rubber, acrylic styrene-butadiene rubber, epoxy resin, nylon, and the like.

In some embodiments, the conductive material includes, but is not limited to: a carbon-based material, a metal-based material, a conductive polymer, or a mixture thereof. In some embodiments, the carbon-based material is selected from natural graphite, artificial graphite, carbon black, acetylene black, Ketjen black, carbon fibers, or any combination thereof. In some embodiments, the metal-based material is selected from metal powder, metal fibers, copper, nickel, aluminum, and silver. In some embodiments, the conductive polymer is a polyphenylene derivative.

In some embodiments, the current collector includes, but is not limited to: copper foil, nickel foil, stainless steel foil, titanium foil, nickel foam, copper foam, a polymer substrate coated with a conductive metal, and any combination thereof.

The negative electrode can be prepared by using a preparation method known in the art. For example, the negative electrode may be obtained by using the following method: mixing an active material, a conductive material, and a binder in a solvent to prepare an active material composition, and applying the active material composition on a current collector. In some embodiments, the solvent may include, but is not limited to, water and the like.

3. Positive Electrode

The positive electrode used in the electrochemical apparatus of this application may be prepared by using materials, constructions and manufacturing methods well known in the art. In some embodiments, the positive electrode of this application may be prepared by using the technology described in U.S. Pat. No. 9,812,739B, which is incorporated herein by reference in its entirety.

In some embodiments, the positive electrode includes a positive electrode current collector and a positive active material layer on the current collector. In some embodiments, the positive active material layer includes a positive active material, and the positive active material includes at least one lithiated intercalation compound that reversibly intercalates and deintercalates lithium ions. In some embodiments, the positive active material includes a composite oxide. In some embodiments, the composite oxide contains lithium and at least one element selected from cobalt, manganese and nickel.

In some embodiments, the positive active material is selected from lithium cobaltate ($LiCoO_2$), a lithium nickel cobalt manganese (NCM) ternary material, lithium iron phosphate ($LiFePO_4$), lithium manganate ($LiMn_2O_4$), or any combination thereof.

In some embodiments, the positive active material includes a lithium cobalt oxide, the lithium cobalt oxide includes an element M, and the element M is selected from one or more of Mg, Ti, Al, Zr, Sn, Zn, or Ca.

In some embodiments, based on a total weight of the positive active material, a weight percentage of the element M is 0.005 wt % to 1 wt %. In some embodiments, based on the total weight of the positive active material, the element M is 0.005 wt %, 0.007 wt %, 0.009 wt %, 0.01 wt %, 0.03 wt %, 0.05 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt %, or in a range defined by any two of these values.

In some embodiments, the positive active material is an aggregate. In some embodiments, a primary particle size of the positive active material is 200 nm to 3000 nm. In some embodiments, the primary particle size of the positive active material is 200 nm, 300 nm, 500 nm, 600 nm, 800 nm, 1000 nm, 1500 nm, 2000 nm, 2200 nm, 2500 nm, or 3000 nm, or in a range defined by any two of these values.

In some embodiments, a secondary particle size of the positive active material is 5 µm to 15 µm. In some embodiments, the secondary particle size of the positive active material is 5 µm, 6 µm, 8 µm, 10 µm, 12 µm, 14 µm, or 15 µm, or in a range defined by any two of these values.

In some embodiments, a specific surface area of the positive active material is 0.9 $m^2$/g to 1.5 $m^2$/g. In some embodiments, the specific surface area of the positive active material is 0.9 $m^2$/g, 1.2 $m^2$/g, 1.3 $m^2$/g, 1.4 $m^2$/g, or 1.5 $m^2$/g, or in a range defined by any two of these values.

In some embodiments, the positive active material may have a coating on its surface, or may be mixed with another compound having a coating. The coating may include at least one coating element compound selected from an oxide of a coating element, a hydroxide of a coating element, an oxyhydroxide of a coating element, an oxycarbonate of a coating element, and a hydroxycarbonate of a coating element. The compound used in the coating may be amorphous or crystalline.

In some embodiments, the coating element contained in the coating may include Mg, Co, K, Na, Ca, Si, Ti, V, Sn, Ge, Ga, B, As, Zr, F, or any combination thereof. The coating may be applied by any method as long as the method does not produce adverse effects on the performance of the positive active material. For example, the method may include any coating method known in the art, such as spraying and dipping.

In some embodiments, the positive active material layer further includes a binder, and optionally includes a conductive material. The binder enhances binding between particles of the positive active material, and binding between the positive active material and the current collector.

In some embodiments, the binder includes, but is not limited to: polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(vinylidene fluoride), polyethylene, polypropylene, styrene-butadiene rubber, acrylic styrene-butadiene rubber, epoxy resin, nylon, and the like.

In some embodiments, the conductive material includes, but is not limited to: a carbon-based material, a metal-based material, a conductive polymer, and a mixture thereof. In some embodiments, the carbon-based material is selected from natural graphite, artificial graphite, carbon black, acetylene black, Ketjen black, carbon fibers, or any combination thereof. In some embodiments, the metal-based material is selected from metal powder, metal fibers, copper, nickel, aluminum, and silver. In some embodiments, the conductive polymer is a polyphenylene derivative.

In some embodiments, the current collector may be, but is not limited to, aluminum.

The positive electrode may be prepared by using a preparation method known in the art. For example, the positive electrode may be obtained by using the following method: mixing an active material, a conductive material, and a binder in a solvent to prepare an active material composition, and applying the active material composition on a current collector. In some embodiments, the solvent may include, but is not limited to, N-methylpyrrolidone and the like.

In some embodiments, the positive electrode is prepared from a positive electrode material formed using a positive active material layer including lithium transition metal series compound powder and a binder on the current collector.

In some embodiments, the positive active material layer usually can be prepared by the following operations: a positive electrode material and a binder (a conductive material and a thickener used as required) are mixed by using a dry process to form a sheet, and the obtained sheet is connected to a positive electrode current collector by pressing, or these materials are dissolved or dispersed in a liquid medium to form a slurry, and the slurry is coated on the positive electrode current collector and dried. In some embodiments, the material of the positive active material layer includes any material known in the art.

4. Separator

In some embodiments, the electrochemical apparatus according to this application has a separator disposed between the positive electrode and the negative electrode to prevent short circuit. The separator used in the electrochemical apparatus according to this application is not particularly limited to any material or shape, and may be based on any technology disclosed in the prior art. In some embodiments, the separator includes a polymer or an inorganic substance formed by a material stable to the electrolyte of this application.

For example, the separator may include a substrate layer and a surface finishing layer. The substrate layer is a non-woven fabric, membrane, or composite membrane having a porous structure, and a material of the substrate layer is selected from at least one of polyethylene, polypropylene, polyethylene glycol terephthalate, and polyimide. Specifically, a polypropylene porous membrane, a polyethylene porous membrane, polypropylene non-woven fabric, polyethylene non-woven fabric, or polypropylene-polyethylene-polypropylene porous composite membrane can be selected.

The surface finishing layer is provided on at least one surface of the substrate layer, the surface finishing layer may be a polymer layer or an inorganic substance layer or a layer formed by mixing a polymer with an inorganic substance, a ratio of a thickness of the substrate layer to a thickness of the surface finishing layer is 1:1 to 20:1, the thickness of the substrate layer is 4 μm to 14 μm, and the thickness of the surface finishing layer is 1 μm to 5 μm.

The inorganic layer includes inorganic particles and a binder. The inorganic particles are selected from one or a combination of aluminum oxide, silicon oxide, magnesium oxide, titanium oxide, hafnium oxide, tin oxide, ceria oxide, nickel oxide, zinc oxide, calcium oxide, zirconium oxide, yttrium oxide, silicon carbide, boehmite, aluminum hydroxide, magnesium hydroxide, calcium hydroxide, and barium sulfate.

The binder is selected from one or a combination of a polyvinylidene fluoride, a vinylidene fluoride-hexafluoropropylene copolymer, a polyamide, a polyacrylonitrile, a polyacrylate, a polyacrylic acid, a polyacrylate, a polyvinylpyrrolidone, a polyvinyl ether, a polymethyl methacrylate, a polytetrafluoroethylene, and a polyhexafluoropropylene. The polymer layer includes a polymer, and a material of the polymer includes at least one of polyamide, polyacrylonitrile, an acrylate polymer, polyacrylic acid, a polyacrylate, a polyvinylpyrrolidone, a polyvinyl ether, a polyvinylidene fluoride, or a poly(vinylidene fluoride-hexafluoropropylene).

IV. Application

The electrolyte according to the embodiments of this application can be used for reducing the storage resistance and cycle resistance of a battery and improving the overcharge performance and hot box performance of the battery, and is suitable for being used in an electronic device containing an electrochemical apparatus.

The electrochemical apparatus according to this application is not particularly limited to any purpose, and may be used for any known purposes. For example, the electrochemical apparatus may be used for a notebook computer, a pen-input computer, a mobile computer, an electronic book player, a portable telephone, a portable fax machine, a portable copier, a portable printer, a headset, a video recorder, a liquid crystal television, a portable cleaner, a portable CD player, a mini-disc, a transceiver, an electronic notebook, a calculator, a storage card, a portable recorder, a radio, a standby power source, a motor, an automobile, a motorcycle, a motor bicycle, a bicycle, a lighting appliance, a toy, a game console, a clock, an electric tool, a flash lamp, a camera, a large household battery, a lithium-ion capacitor, or the like.

Hereinafter, the preparation and performance of the lithium-ion battery according to this application are illustrated by taking the lithium-ion battery as an example and in conjunction with specific examples of preparing the electrolyte according to this application and methods for testing the electrochemical apparatus. It would be understood by those skilled in the art that the preparation methods described in this application are only examples, and any other suitable preparation methods are within the scope of this application.

Although the lithium-ion battery is exemplified, a person skilled in the art could conceive that the positive electrode material of this application may be used in other suitable electrochemical apparatuses after reading this application. Such electrochemical apparatuses include any apparatus in which an electrochemical reaction takes place. Specific examples of the apparatus include all kinds of primary batteries, secondary batteries, fuel batteries, solar batteries, or capacitors. Especially, the electrochemical apparatus is a lithium secondary battery, including a lithium metal secondary battery, a lithium-ion secondary battery, a lithium polymer secondary battery, or a lithium-ion polymer secondary battery.

EXAMPLES

Below, this application will be further specifically described with examples and comparative examples, and this application is not limited to these examples as long as the essence of this application is not changed.
1. Preparation of a Lithium-Ion Battery
(1) Preparation of an Electrolyte In a glove box under argon atmosphere with a water content less than 10 ppm, ethylene carbonate (EC for short), diethyl carbonate (DEC for short), and propylene carbonate (PC for short) were mixed uniformly in a weight ratio of 3:4:3, and a fully dried lithium salt $LiPF_6$ was dissolved in the mixed solvent to obtain a base electrolyte, where a concentration of $LiPF_6$ in the base electrolyte was 1 mol/L. Different contents of substances as shown in Tables 2 and 3 below were added to the base electrolyte to obtain electrolytes of different examples and comparative examples. The contents of the substances in the electrolytes described below were calculated based on total weights of the electrolytes.

Specific examples of the compound of formula 1 are as follows:

formula 1-1
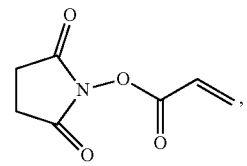

formula 1-2
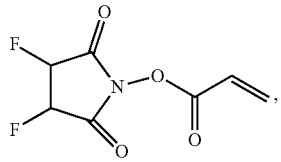

formula 1-3
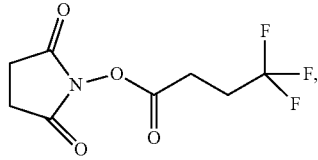

formula 1-5
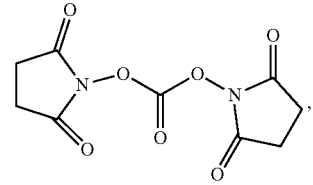

-continued formula 1-6
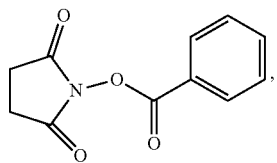

formula 1-7
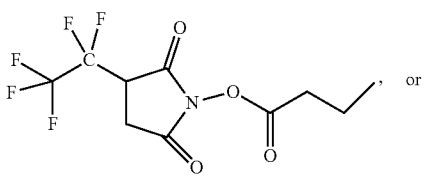
, or formula 1-11
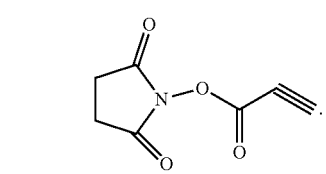

Specific examples of the nitrile compound are as follows:

formula 2-1
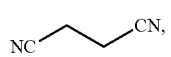

formula 2-3
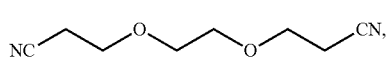

formula 4-1
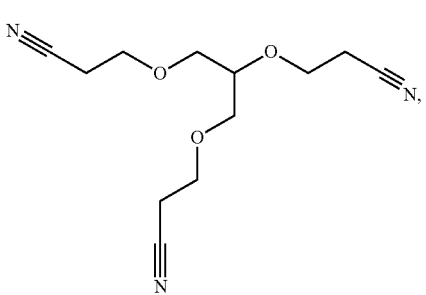

formula 5-1
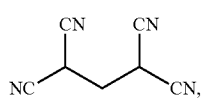

formula 5-2
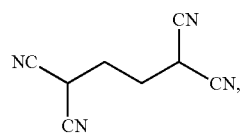

formula 5-3
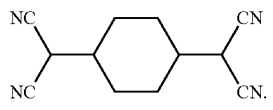

Specific examples of the fluorosulfonic anhydride compound are as follows:

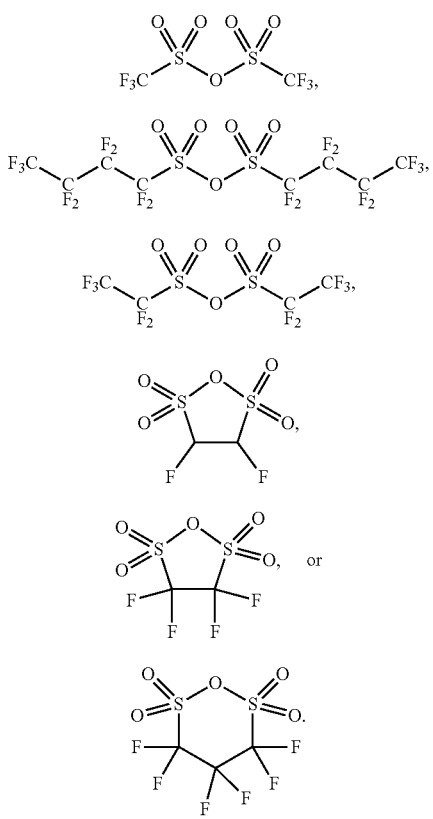

formula 6-1 formula 6-2 formula 6-3 formula 6-4 formula 6-5 formula 6-6

2) Preparation of a Positive Electrode
Preparation of a Positive Electrode 1:

(1) Lithium carbonate, 10 μm cobalt oxide and magnesium oxide were mixed in a supermixer by a dry way in a molar ratio of lithium atoms: (cobalt atoms+magnesium atoms) of 1:1, where the modification element Mg accounted for 0.01 wt % of the finally generated small-particle lithium cobaltate sample, the mixing speed was 2700 rpm, and the mixing time was 3 minutes; after the mixing was completed, the materials were put into a roasting furnace for roasting at 600° C. for 10 hours, the roasted materials were coarsely crushed and then crushed by means of an air-flow mill to finally obtain a small-particle lithium cobaltate sample with a primary particle size of about 350 nm and a secondary particle size of about 9 μm; and (2) The small-particle lithium cobaltate serving as a positive active material obtained in step (1), acetylene black serving as a conductive agent, and polyvinylidene fluoride (PVDF for short) serving as a binder were thoroughly mixed in an appropriate amount of N-methyl pyrrolidone (NMP for short) solvent in a weight ratio of 96:2:2 to form a uniform positive slurry; and the slurry was applied on an aluminum foil of a positive current collector, and drying and cold pressing were performed to obtain the positive electrode.

Preparation of a Positive Electrode 2:

(1) Lithium hydroxide, 3 μm cobalt hydroxide and nano-alumina were mixed in a supermixer by a dry way in a molar ratio of lithium atoms: (cobalt atoms+aluminum atoms) of 1.005:1, where the modification element Al accounted for 0.1 wt % of the finally generated small-particle lithium cobaltate sample, the mixing speed was 1500 rpm, and the mixing time was 4 minutes; after the mixing was completed, the materials were put into a roasting furnace for roasting at 1000° C. for 10 hours, the roasted materials were coarsely crushed and then crushed by means of an air-flow mill to finally obtain a small-particle lithium cobaltate sample with a primary particle size of about 500 nm and a secondary particle size of about 7 μm; and (2) This step was the same as step (2) in the preparation method of the positive electrode 1.

Preparation of a Positive Electrode 3:

(1) Lithium carbonate and cobalt oxide were mixed by means of dry bah milling in a molar ratio of lithium atoms: cobalt atoms of 1.001:1; after the mixing was completed, the materials were put into a roasting furnace for roasting at 1020° C. for 10 hours, the roasted materials were coarsely crushed and then crushed by means of an air-flow mill to finally obtain a small-particle lithium cobaltate sample to be coated with a primary particle size of about 2000 nm and a secondary particle size of about 9 μm; and (2) This step was the same as step (2) in the preparation method of the positive electrode 1.

3) Preparation of a Negative Electrode

Graphite serving as a negative active material, acetylene black serving as a conductive agent, styrene-butadiene rubber (SBR) serving as a binder, and sodium carboxymethyl cellulose (CMC) serving as a thickener were thoroughly mixed in an appropriate amount of deionized water solvent in a weight ratio of 95:2:2:1 to form a uniform negative slurry; and the slurry was applied on a Cu foil of a negative current collector, and drying and cold pressing were performed to obtain a negative active material layer, followed by cutting and welding of tabs to obtain the negative electrode.

4) Separator: a PE porous polymer film was used as the separator.

5) Preparation of a lithium-ion battery: the positive electrode, the separator, and the negative electrode were laid in order with the separator between the positive electrode and the negative electrode for isolation, and then wound and placed in an outer packaging foil, the prepared electrolyte was injected into a dried battery, and the preparation of the lithium-ion battery was completed after processes such as vacuum packaging, standing, chemical conversion, and shaping.

2. Performance Test Methods of the Lithium-Ion Battery (1) Test on High-Temperature Capacity Retention Rate:

1) At 45° C., the battery was discharged to 3.0 V at 0.2 C and placed for 3 minutes, and then charged to 4.45 V at 0.7 C, charged to 0.025 C at the constant voltage of 4.45 V, and placed for 5 minutes; 2) step 1) was repeated twice; 3) at 45° C., the battery was discharged to 3.0 V at 1 C and placed for 3 minutes, and then charged to 4.45 V at 0.7 C, charged to 0.025 C at the constant voltage of 4.45 V, and placed for 5 minutes; 4) step 3) was repeated 48 times; and 5) steps 1) and 3) were repeated until a cycle ended. This was as a charging and discharging cycle. The capacity retention rate after the cycle of the battery was calculated:

Capacity retention rate of the lithium-ion battery after $N$ cycles (%)=Discharge capacity at the $N$-th cycle/Discharge capacity at the first cycle× 100%.

(2) Test on Room-Temperature Capacity Retention Rate:

1) At 25° C., the battery was discharged to 3.0 V at 0.2 C and placed for 3 minutes, and then charged to 4.45 V at 0.7 C, charged to 0.025 C at the constant voltage of 4.45 V, and placed for 5 minutes; 2) step 1) was repeated twice; 3) at 25°

C., the battery was discharged to 3.0 V at 1 C and placed for 3 minutes, and then charged to 4.45 V at 0.7 C, charged to 0.025 C at the constant voltage of 4.45 V, and placed for 5 minutes; 4) step 3) was repeated 48 times; and 5) steps 1) and 3) were repeated until a cycle ended. This was as a charging and discharging cycle. The capacity retention rate after the cycle of the battery was calculated:

Capacity retention rate of the lithium-ion battery after $N$ cycles (%)=Discharge capacity at the $N$-th cycle/Discharge capacity at the first cycle× 100%.

(3) Test on High-Temperature Storage Performance:

At 25° C., the lithium-ion battery was stood for 30 minutes, then charged to 4.45 V at a constant current rate of 0.5 C, charged to 0.05 C at the constant voltage of 4.45 V, stood for 5 minutes, and stored for 24 days at 85° C., the thickness of the battery was measured, and the thickness swelling rate of the battery was calculated by means of the following equation:

Thickness swelling rate=[(Thickness after storage−Thickness before storage)/Thickness before storage]×100%.

Relevant performance parameters of lithium cobaltate serving as a positive active material used in the positive electrodes 1 to 3 were shown in Table 1.

TABLE 1

|  | Primary particle size (nm) | Secondary particle size (μm) | pH | Specific surface area (m²/g) |
|---|---|---|---|---|
| Positive electrode 1 | 350 | 9 | 10.34 | 1.06 |
| Positive electrode 2 | 500 | 7 | 10.18 | 1.22 |
| Positive electrode 3 | 2000 | 9 | 10.61 | 0.46 |

As can be seen from Table 1, the active materials in both the positive electrode 1 and the positive electrode 2 were ultra-small-particle lithium cobaltate having a nano-scale primary particle size, and the primary particle size of small-particle lithium cobaltate serving as an active material in the positive electrode 3 was a micron size. In addition, the small-particle lithium cobaltate samples had lower pH values, this type of lithium cobaltate samples had better electrical properties, and the specific surface area of the small-particle lithium cobaltate was larger.

A. The electrolytes and lithium-ion batteries of Examples 1 to 39 and Comparative Examples 1 to 3 were prepared according to the above preparation methods. The contents of relevant substances in the electrolytes and performance parameters were shown in Table 2.

TABLE 2

|  | Type of positive electrode | Type and content of compound of formula 1 | Type and content of nitrile compound | Capacity retention rate after 500 cycles at 45° C. | Capacity retention rate after 500 cycles at 25° C. | Storage thickness swelling rate at 85° C. |
|---|---|---|---|---|---|---|
| Comparative Example 1 | Positive electrode 1 | — | — | 60.3% | 70.2% | 40% |
| Comparative Example 2 | Positive electrode 1 | — | Formula 2-3: 3 wt % | 69.6% | 75.1% | 25.6% |
| Comparative Example 3 | Positive electrode 2 | — | Formula 4-1: 3 wt % | 70.5% | 75.3% | 28% |
| Example 1 | Positive electrode 1 | Formula 1-1: 0.3 wt % | — | 77.2% | 83.2% | 25.7% |
| Example 2 | Positive electrode 2 | Formula 1-5: 0.3 wt % | — | 76.9% | 83.6% | 24.8% |
| Example 3 | Positive electrode 2 | Formula 1-6: 0.3 wt % | — | 75.5% | 82.3% | 24.1% |
| Example 4 | Positive electrode 3 | Formula 1-6: 0.3 wt % | — | 74.5% | 78.3% | 23.3% |
| Example 5 | Positive electrode 1 | Formula 1-5: 0.1 wt % | — | 74.1% | 81.3% | 26.2% |
| Example 6 | Positive electrode 1 | Formula 1-5: 0.3 wt % | — | 78.4% | 84.2% | 25.2% |
| Example 7 | Positive electrode 1 | Formula 1-5: 0.5 wt % | — | 78.1% | 84.1% | 25.3% |
| Example 8 | Positive electrode 1 | Formula 1-5: 1 wt % | — | 78.0% | 83.9% | 24.9% |
| Example 9 | Positive electrode 1 | Formula 1-5: 2 wt % | — | 77.3% | 82.7% | 25.2% |
| Example 10 | Positive electrode 1 | Formula 1-5: 5 wt % | — | 76.9% | 81.5% | 25.4% |
| Example 11 | Positive electrode 1 | Formula 1-1: 0.3 wt % | Formula 2-3: 3 wt % | 87.1% | 96.5% | 11.7% |
| Example 12 | Positive electrode 1 | Formula 1-1: 0.3 wt % | Formula 4-1: 2 wt % | 87.3% | 96.1% | 11.4% |
| Example 13 | Positive electrode 1 | Formula 1-1: 0.3 wt % | Formula 5-2: 2 wt % | 86.9% | 96.2% | 11.9% |
| Example 14 | Positive electrode 1 | Formula 1-5: 0.3 wt % | Formula 2-3: 3 wt % | 86.4% | 95.9% | 12.2% |
| Example 15 | Positive electrode 1 | Formula 1-5: 0.3 wt % | Formula 4-1: 2 wt % | 86.3% | 95.7% | 12.5% |
| Example 16 | Positive electrode 1 | Formula 1-5: 0.3 wt % | Formula 5-2: 2 wt % | 87.6% | 96.8% | 12.7% |

TABLE 2-continued

| | Type of positive electrode | Type and content of compound of formula 1 | Type and content of nitrile compound | Capacity retention rate after 500 cycles at 45° C. | Capacity retention rate after 500 cycles at 25° C. | Storage thickness swelling rate at 85° C. |
|---|---|---|---|---|---|---|
| Example 17 | Positive electrode 1 | Formula 1-5: 0.1 wt % | Formula 2-3: 2 wt % + Formula 4-1: 1 wt % | 87.9% | 96.9% | 10.1% |
| Example 18 | Positive electrode 1 | Formula 1-5: 0.5 wt % | Formula 2-3: 2 wt % + Formula 4-1: 1 wt % | 88.1% | 97.1% | 9.9% |
| Example 19 | Positive electrode 1 | Formula 1-5: 2 wt % | Formula 2-3: 2 wt % + Formula 4-1: 1 wt % | 88.2% | 97.2% | 9.6% |
| Example 20 | Positive electrode 1 | Formula 1-5: 4 wt % | Formula 2-3: 2 wt % + Formula 4-1: 1 wt % | 88.3% | 96.7% | 9.5% |
| Example 21 | Positive electrode 1 | Formula 1-5: 5 wt % | Formula 2-3: 2 wt % + Formula 4-1: 1 wt % | 88.1% | 97.3% | 9.7% |
| Example 22 | Positive electrode 1 | Formula 1-5: 8 wt % | Formula 2-3: 2 wt % + Formula 4-1: 1 wt % | 87.8% | 96.9% | 10.0% |
| Example 23 | Positive electrode 3 | formula 1-5: 5 wt % | Formula 2-3: 2 wt % + Formula 4-1: 1 wt % | 80.5% | 92.4% | 10.4% |
| Example 24 | Positive electrode 2 | Formula 1-5: 10 wt % | Formula 2-3: 2 wt % + Formula 4-1: 1 wt % | 85.1% | 95.0% | 13.1% |
| Example 25 | Positive electrode 2 | Formula 1-5: 0.3 wt % | Formula 2-1: 3 wt % | 87.1% | 96.5% | 11.7% |
| Example 26 | Positive electrode 2 | Formula 1-5: 0.3 wt % | Formula 2-3: 2 wt % | 87.3% | 96.1% | 11.4% |
| Example 27 | Positive electrode 2 | Formula 1-5: 0.3 wt % | Formula 5-1: 2 wt % | 86.9% | 96.2% | 11.9% |
| Example 28 | Positive electrode 2 | Formula 1-5: 0.3 wt % | Formula 2-1: 2 wt % + Formula 5-1: 1 wt % | 87.9% | 96.9% | 10.1% |
| Example 29 | Positive electrode 2 | Formula 1-5: 0.3 wt % | Formula 2-2: 2 wt % + Formula 5-1:1 wt % | 88.1% | 97.1% | 9.9% |
| Example 30 | Positive electrode 2 | Formula 1-5: 0.3 wt % | Formula 2-1: 1 wt % + Formula 5-1: 2 wt % | 88.2% | 97.2% | 9.6% |
| Example 31 | Positive electrode 2 | Formula 1-5: 0.3 wt % | Formula 2-1: 1 wt % + Formula 5-3: 2 wt % | 88.3% | 96.7% | 9.5% |
| Example 32 | Positive electrode 2 | Formula 1-5: 0.3 wt % | Formula 2-1: 2 wt % + Formula 5-3: 2 wt % | 88.1% | 97.3% | 9.7% |
| Example 33 | Positive electrode 2 | Formula 1-5: 0.3 wt % | Formula 2-1: 4 wt % + Formula 5-3: 2 wt % | 87.8% | 96.9% | 10.0% |
| Example 34 | Positive electrode 2 | Formula 1-5: 0.3 wt % | Formula 2-1: 3 wt % + Formula 2-2: 1 wt % + Formula 2-3: 4 wt % | 85.1% | 94.2% | 13.5% |
| Example 35 | Positive electrode 2 | Formula 1-5: 0.3 wt % | Formula 2-1: 7 wt % + Formula 2-3: 3 wt % | 84.7% | 93.5% | 14.5% |

TABLE 2-continued

|  | Type of positive electrode | Type and content of compound of formula 1 | Type and content of nitrile compound | Capacity retention rate after 500 cycles at 45° C. | Capacity retention rate after 500 cycles at 25° C. | Storage thickness swelling rate at 85° C. |
|---|---|---|---|---|---|---|
| Example 36 | Positive electrode 2 | Formula 1-3: 0.3 wt % | Formula 2-1: 7 wt % + Formula 2-3: 5 wt % | 85.1% | 93.9% | 13.1% |
| Example 37 | Positive electrode 2 | Formula 1-2: 0.3 wt % | Formula 2-2: 2 wt % + Formula 5-3: 1 wt % | 88.1% | 97.1% | 9.9% |
| Example 38 | Positive electrode 2 | Formula 1-7: 0.3 wt % | Formula 2-2: 2 wt % + Formula 5-3: 1 wt % | 88.2% | 97.2% | 9.6% |
| Example 39 | Positive electrode 2 | Formula 1-11: 0.3 wt % | Formula 2-3: 3 wt % | 85.1% | 88.7% | 15.9% |

"—" indicates that such substance was not added.

Since the compound of formula 1 and the nitrile compound were not added to the electrolyte of Comparative Example 1, it can be seen that the high-temperature cycle performance of the lithium-ion battery prepared therefrom was poor, and the high-temperature storage performance thereof deteriorated seriously.

As can be seen from the test results of Examples 1-10 and Comparative Examples 2-3, the addition of the compound of formula 1 or the nitrile compound of a specific structure to the electrolyte improved both the high-temperature/room-temperature cycle performance and the high-temperature storage performance to certain extent.

As can be seen from the test results of Examples 11 to 39, the addition of the compound of formula 1 and the nitrile compound of a specific structure to the electrolyte can significantly improve both the high-temperature/room-temperature cycle performance and the high-temperature storage performance. Without being bound by a particular theory, this may be because the reduction of the compound of formula 1 at the negative electrode to form a stable negative electrode protective film reduced side reactions of the electrolyte at the negative electrode, and the small resistance of the formed SEI film can reduce the consumption of the electrolyte in the battery, thereby improving the cycle performance and high-rate discharge performance of the lithium-ion battery. The nitrile compound of the specific structure can be made complex with a transition metal on the surface of the positive electrode, which reduced the dissolution of the transition metal, reduced the contact between the electrolyte and the positive electrode, and further reduced the side reactions of the electrolyte at a high temperature, thereby improving the cycle performance and the high-temperature storage performance.

As can be seen from the test results of Examples 3 to 4, in the case where the electrolyte contained the compound of formula 1, when the positive electrode used the small-particle positive active material, the cycle performance and high-temperature storage performance of the battery were improved to certain extent.

As can be seen from the test results of Comparative Example 4, Example 22 and Example 23, in the case where the electrolyte contained both the compound of formula 1 and the nitrile compound, when the positive electrode used the small-particle positive active material, the cycle performance and high-temperature storage performance of the battery can be further improved.

B. The electrolytes and lithium-ion batteries of Examples 40 to 51 in Table 3 were prepared according to the above preparation methods. The contents of relevant substances in the electrolytes and performance parameters were shown in Table 3.

TABLE 3

|  | Type of positive electrode | Type and content of compound of formula 1 | Type and content of nitrile compound | Type and content of fluorosulfonic anhydride compound | Capacity retention rate after 500 cycles at 45° C. | Capacity retention rate after 500 cycles at 25° C. | Storage thickness swelling rate at 85° C. |
|---|---|---|---|---|---|---|---|
| Example 6 | Positive electrode 1 | Formula 1-5: 0.3 wt % | — | — | 78.4% | 84.2% | 25.2% |
| Example 18 | Positive electrode 1 | Formula 1-5: 0.5 wt % | Formula 2-3: 2 wt % + Formula 4-1: 1 wt % | — | 88.1% | 97.1% | 9.9% |
| Example 40 | Positive electrode 1 | Formula 1-5: 0.5 wt % | — | Formula 6-1: 0.1 wt % | 87.0% | 95.0% | 15.0% |
| Example 41 | Positive electrode 1 | Formula 1-5: 0.5 wt % | — | Formula 6-1: 0.5 wt % | 87.2% | 95.4% | 14.5% |

TABLE 3-continued

| | Type of positive electrode | Type and content of compound of formula 1 | Type and content of nitrile compound | Type and content of fluorosulfonic anhydride compound | Capacity retention rate after 500 cycles at 45° C. | Capacity retention rate after 500 cycles at 25° C. | Storage thickness swelling rate at 85° C. |
|---|---|---|---|---|---|---|---|
| Example 42 | Positive electrode 1 | Formula 1-5: 0.5 wt % | — | Formula 6-1: 1 wt % | 87.5% | 95.8% | 14.0% |
| Example 43 | Positive electrode 1 | Formula 1-5: 0.5 wt % | — | Formula 6-1: 3 wt % | 88.0% | 96.2% | 13.5% |
| Example 44 | Positive electrode 1 | Formula 1-5: 0.5 wt % | — | Formula 6-1: 5 wt % | 88.3% | 96.5% | 13.5% |
| Example 45 | Positive electrode 1 | Formula 1-5: 0.3 wt % | Formula 2-3: 2 wt % + Formula 4-1: 1 wt % | Formula 6-1: 0.5 wt % | 89.5% | 98.7% | 9.0% |
| Example 46 | Positive electrode 1 | Formula 1-5: 0.3 wt % | Formula 2-3: 2 wt % + Formula 4-1: 1 wt % | Formula 6-1: 1 wt % | 89.3% | 98.4% | 8.9% |
| Example 47 | Positive electrode 1 | Formula 1-5: 0.3 wt % | Formula 2-3: 2 wt % + Formula 4-1: 1 wt % | Formula 6-2: 0.5 wt % | 89.0% | 98.0% | 9.0% |
| Example 48 | Positive electrode 2 | Formula 1-5: 0.3 wt % | Formula 2-3: 2 wt % + Formula 4-1: 1 wt % | Formula 6-5: 0.5 wt % | 88.9% | 97.8% | 9.3% |
| Example 49 | Positive electrode 2 | Formula 1-1: 0.3 wt % | Formula 2-3: 2 wt % + Formula 4-1: 1 wt % | Formula 6-1: 1 wt % | 89.1% | 98.3% | 9.9% |
| Example 50 | Positive electrode 3 | Formula 1-1: 0.3 wt % | Formula 2-3: 2 wt % + Formula 4-1: 1 wt % | Formula 6-1: 1 wt % | 82.1% | 93.3% | 10.1% |

"—" indicates that such substance was not added.

As can be seen from the test results of Examples 40 to 44 and Example 8, the cycle performance of the lithium-ion battery can be significantly improved by adding a fluorosulfonic anhydride compound of a specific structure to the electrolyte containing the compound of formula 1 and the nitrile compound. Without being bound by a particular theory, this may be because the fluorosulfonic anhydride of the specific structure was used as a functional additive, and the filming potential of the additive at the negative electrode was far lower than that of conventional sulfonic anhydride compounds through the strong electron-withdrawing effect of F atoms, thereby the resistance of the SEI film. The current distribution of the battery during charging and discharging was uniform, the polarization was reduced, the room-temperature and low-temperature direct-current internal resistance of the battery was reduced, and the cycle performance of the lithium-ion battery was improved.

As can be seen from the test results of Examples 47, 49 and 50, in the case where the electrolyte contained the compound of formula 1, the nitrile compound of the specific structure and the fluorosulfonic anhydride compound, when the positive electrode used the small-particle positive active material, the cycle performance and high-temperature storage performance of the battery can be further improved.

References to "some embodiments", "other embodiments", "an embodiment", "another example", "examples", "specific examples", or "some examples" in the specification mean the inclusion of specific features, structures, materials, or characteristics described in the embodiment or example in at least one embodiment or example of this application. Accordingly, descriptions appearing in the specification, such as "in some embodiments", "in the embodiments", "in an embodiment", "in another example", "in an example", "in a particular example", or "for example", are not necessarily references to the same embodiments or examples in the application. In addition, specific features, structures, materials, or characteristics herein may be incorporated in any suitable manner into one or more embodiments or examples.

Although illustrative embodiments have been demonstrated and described, those skilled in the art should understand that the above embodiments are not to be construed as limiting the application, and that the embodiments may be changed, replaced, and modified without departing from the spirit, principle, and scope of this application.

What is claimed is:

1. An electrolyte, comprising a compound of formula 1:

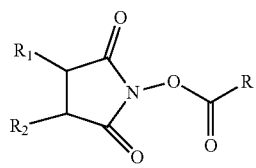

formula 1;
wherein $R_1$ and $R_2$ are each independently selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof;

wherein R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

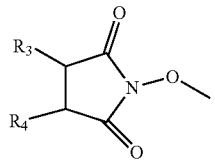

or any combination thereof;

wherein $R_3$ and $R_4$ are each independently selected from H, halogen atom, a substituted or unsubstituted $C_{1-3}$ alkyl group, a substituted or unsubstituted $C_{3-7}$ cycloalkyl group, a substituted or unsubstituted $C_{2-6}$ alkenyl group, a substituted or unsubstituted $C_{2-6}$ alkynyl group, a substituted or unsubstituted $C_{1-6}$ alkoxy group, or any combination thereof;

wherein when the substituent groups are each independently substituted, the substituent group is selected from at least one of halogen atom, a cyano group, a $C_{1-6}$ alkyl group, a $C_{3-6}$ cycloalkyl group, a $C_{1-6}$ alkoxy group, a $C_{2-6}$ alkenyl group, a $C_{6-10}$ aryl group, or a $C_{6-10}$ heteroaryl group;

wherein heteroatoms in the groups each are independently selected from at least one of O, S, N, or P;

wherein the electrolyte further comprises a nitrile compound; and the nitrile compound comprises a compound shown in formula 2, and at least one of a compound shown in formula 4 or a compound shown in formula 5:

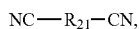

formula 2

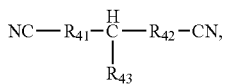

formula 4

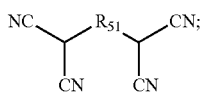

formula 5 wherein $R_{21}$ is selected from a substituted or unsubstituted $C_{1-5}$ alkylidene group or $R^c$—(O—$R^a$)$_A$—O—$R^b$, $R^a$ and $R^b$ are each independently selected from a substituted or unsubstituted $C_{1-3}$ alkylidene group, $R^c$ is selected from a single bonded or a substituted or unsubstituted $C_{1-3}$ alkylidene group, and A is an integer ranging from 0 to 2;

$R_{41}$, $R_{42}$ and $R_{43}$ are each independently selected from a single bonded or a substituted or unsubstituted $C_{1-5}$ alkylidene group, a substituted or unsubstituted $C_{1-5}$ alkyleneoxy group, or any combination thereof;

$R_{51}$ is selected from a substituted or unsubstituted $C_{1-5}$ alkylidene group, a substituted or unsubstituted $C_{3-7}$ cycloalkylidene group, a substituted or unsubstituted $C_{2-10}$ alkenylene group, a substituted or unsubstituted $C_{6-10}$ arylidene group, a substituted or unsubstituted $C_{1-6}$ heterocyclic group, or any combination thereof;

wherein when the substituent groups are each independently substituted, the substituent group is selected from at least one of halogen atom, a nitro group, a cyano group, a carboxyl group, and a sulfate group; and wherein based on a total weight of the electrolyte, the nitrile compound is 0.5 wt % to 10 wt %.

2. The electrolyte according to claim 1, wherein the electrolyte further comprises at least one of the following compounds:

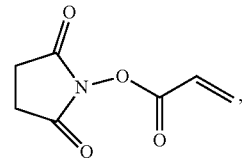

formula 1-1

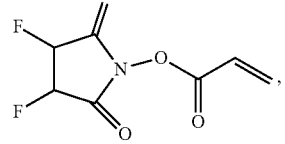

formula 1-2

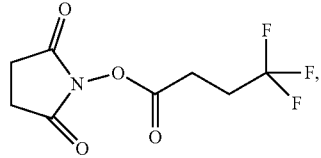

formula 1-3

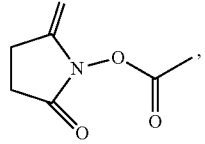

formula 1-4

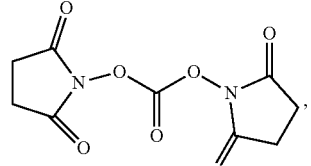

formula 1-5

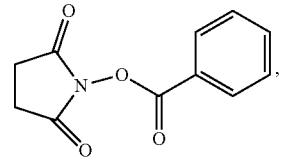

formula 1-6

-continued

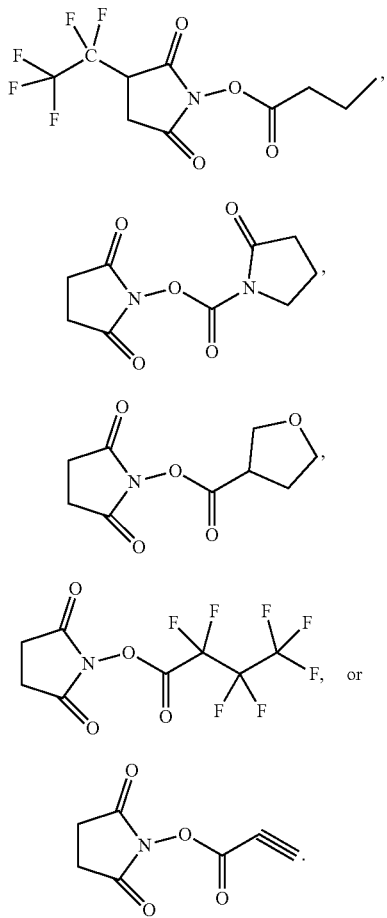

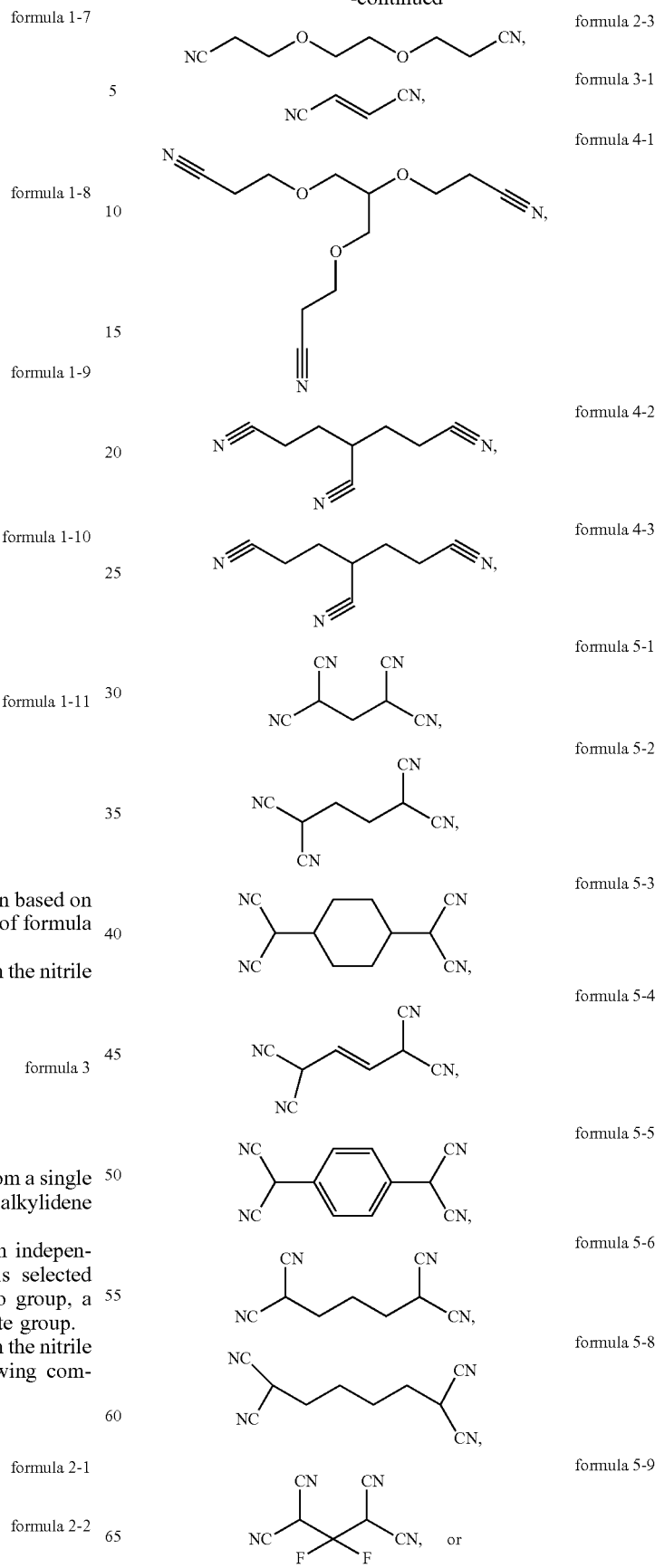

3. The electrolyte according to claim 1, wherein based on the total weight of the electrolyte, the compound of formula 1 is 0.1 wt % to 10 wt %.

4. The electrolyte according to claim 1, wherein the nitrile compound a compound shown in formula 3:

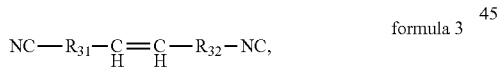

wherein
R$_{31}$ and R$_{32}$ are each independently selected from a single bonded or a substituted or unsubstituted C$_{1-5}$ alkylidene group;
wherein when the substituent groups are each independently substituted, the substituent group is selected from at least one of halogen atom, a nitro group, a cyano group, a carboxyl group, and a sulfate group.

5. The electrolyte according to claim 4, wherein the nitrile compound comprises at least one of the following compounds:

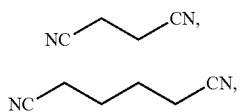

formula 5-10

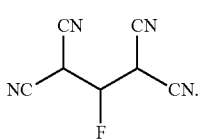

6. The electrolyte according to claim 1, further comprising a fluorosulfonic anhydride compound, and the fluorosulfonic anhydride compound comprises a compound of formula 6:

formula 6

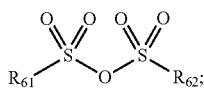

wherein $R_{61}$ and $R_{62}$ are each independently selected from a substituted or unsubstituted $C_{1-6}$ alkyl group, or $R_{61}$ and $R_{62}$ are combined with each other to generate a five- or six-membered ring;

wherein when the substituent groups are each independently substituted, the substituent group is selected from F; and wherein based on the total weight of the electrolyte, the fluorosulfonic anhydride compound is 0.1 wt % to 5 wt %.

7. The electrolyte according to claim 6, wherein the fluorosulfonic anhydride compound comprises at least one of the following compounds:

formula 6-1

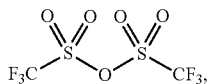

formula 6-2

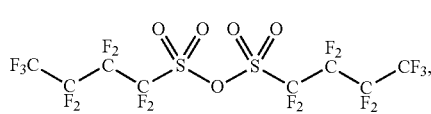

formula 6-3

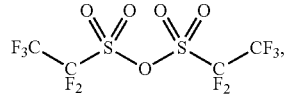

formula 6-4

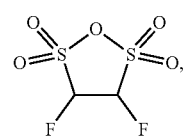

formula 6-5

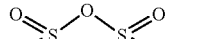

or formula 6-6

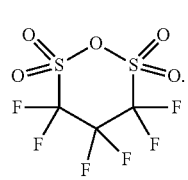

8. An electrochemical apparatus, comprising:
a positive electrode, the positive electrode comprising a positive active material;
a negative electrode, the negative electrode comprising a negative active material; and
an electrolyte, comprising a compound of formula 1:

formula 1

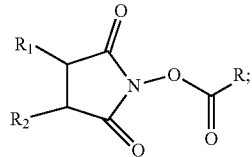

wherein $R_1$ and $R_2$ are each independently selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof;

wherein R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

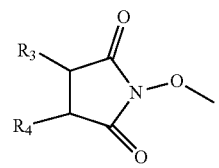

or any combination thereof;

wherein $R_3$ and $R_4$ are each independently selected from H, halogen atom, a substituted or unsubstituted $C_{1-3}$ alkyl group, a substituted or unsubstituted $C_{3-7}$ cycloalkyl group, a substituted or unsubstituted $C_{2-6}$ alkenyl group, a substituted or unsubstituted $C_{2-6}$ alkynyl group, a substituted or unsubstituted $C_{1-6}$ alkoxy group, or any combination thereof;

wherein when the substituent groups are each independently substituted, the substituent group is selected from at least one of halogen atom, a cyano group, a $C_{1-6}$ alkyl group, a $C_{3-6}$ cycloalkyl group, a $C_{1-6}$ alkoxy group, a $C_{2-6}$ alkenyl group, a $C_{6-10}$ aryl group, or a $C_{6-10}$ heteroaryl group; and wherein heteroatoms in the groups each are independently selected from at least one of O, S, N, or P;

wherein the electrolyte further comprises a nitrile compound; and the nitrile compound comprises a compound shown in formula 2, and at least one of a compound shown in formula 4 or a compound shown in formula 5:

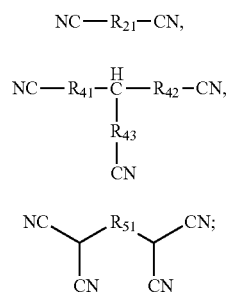

formula 2
$$NC-R_{21}-CN,$$

formula 4
$$NC-R_{41}-\overset{H}{\underset{R_{43}}{C}}-R_{42}-CN,$$

formula 5
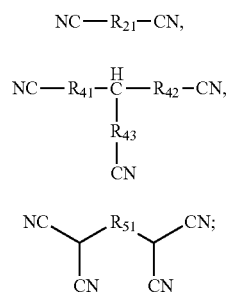

wherein $R_{21}$ is selected from a substituted or unsubstituted $C_{1-5}$ alkylidene group or $R^c-(O-R^a)_A-O-R^b$, $R^a$ and $R^b$ are each independently selected from a substituted or unsubstituted $C_{1-3}$ alkylidene group, $R^c$ is selected from a single bonded or a substituted or unsubstituted $C_{1-3}$ alkylidene group, and A is an integer ranging from 0 to 2;

$R_{41}$, $R_{42}$ and $R_{43}$ are each independently selected from a single bonded or a substituted or unsubstituted $C_{1-5}$ alkylidene group, a substituted or unsubstituted $C_{1-5}$ alkyleneoxy group, or any combination thereof;

$R_{51}$ is selected from a substituted or unsubstituted $C_{1-5}$ alkylidene group, a substituted or unsubstituted $C_{3-7}$ cycloalkylidene group, a substituted or unsubstituted $C_{2-10}$ alkenylene group, a substituted or unsubstituted $C_{6-10}$ arylidene group, a substituted or unsubstituted $C_{1-6}$ heterocyclic group, or any combination thereof;

wherein when the substituent groups are each independently substituted, the substituent group is selected from at least one of halogen atom, a nitro group, a cyano group, a carboxyl group, and a sulfate group; and wherein based on a total weight of the electrolyte, the nitrile compound is 0.5 wt % to 10 wt %.

9. The electrochemical apparatus according to claim 8, wherein the electrolyte further comprises at least one of the following compounds:

formula 1-1
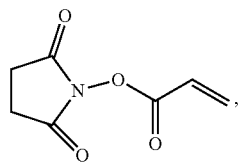

formula 1-2
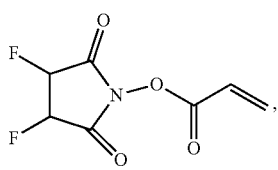

formula 1-3
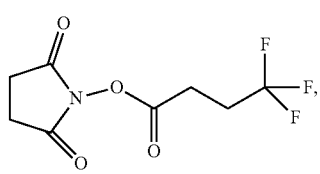

formula 1-4
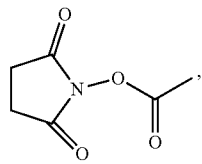

formula 1-5
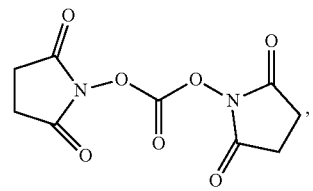

formula 1-6
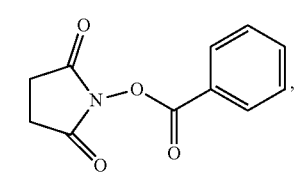

formula 1-7
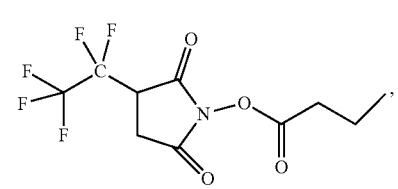

formula 1-8
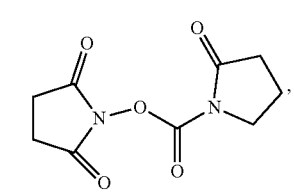

formula 1-9
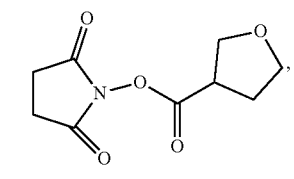

formula 1-10
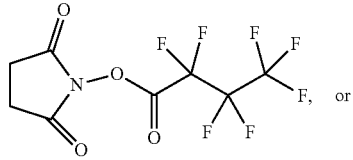

formula 1-11
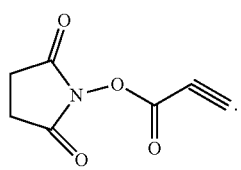

10. The electrochemical apparatus according to claim 8, wherein based on the total weight of the electrolyte, the compound of formula 1 is 0.1 wt % to 10 wt %.

11. The electrochemical apparatus according to claim 8, wherein the nitrile compound further comprises a compound shown in formula 3:

$$NC-R_{31}-\underset{H}{C}=\underset{H}{C}-R_{32}-NC,\quad \text{formula 3}$$

wherein $R_{31}$ and $R_{32}$ are each independently selected from a single bonded or a substituted or unsubstituted $C_{1-5}$ alkylidene group wherein when the substituent groups are each independently substituted, the substituent group is selected from at least one of halogen atom, a nitro group, a cyano group, a carboxyl group, and a sulfate group.

12. The electrochemical apparatus according to claim 11, wherein based on the total weight of the electrolyte, the nitrile compound is 0.5 wt % to 10 wt %.

13. The electrochemical apparatus according to claim 11, wherein the nitrile compound comprises at least one of the following compounds:

formula 2-1 formula 2-2 formula 2-3 formula 3-1 formula 4-1 formula 4-2 formula 4-3 formula 5-1 formula 5-2 formula 5-3 formula 5-4 formula 5-5 formula 5-6 formula 5-8 formula 5-9 formula 5-10

14. The electrochemical apparatus according to claim 8, wherein the electrolyte further comprises a fluorosulfonic anhydride compound, and the fluorosulfonic anhydride compound comprises a compound of formula 6:

$$\text{formula 6}$$

wherein $R_{61}$ and $R_{62}$ are each independently selected from a substituted or unsubstituted $C_{1-6}$ alkyl group, or $R_{61}$ and $R_{62}$ are combined with each other to generate a five- or six-membered ring;

wherein when the substituent groups are each independently substituted, the substituent group is selected from F.

15. The electrochemical apparatus according to claim 14, wherein based on the total weight of the electrolyte, the fluorosulfonic anhydride compound is 0.1 wt % to 5 wt %.

16. The electrochemical apparatus according to claim 14, wherein the fluorosulfonic anhydride compound comprises at least one of the following compounds:

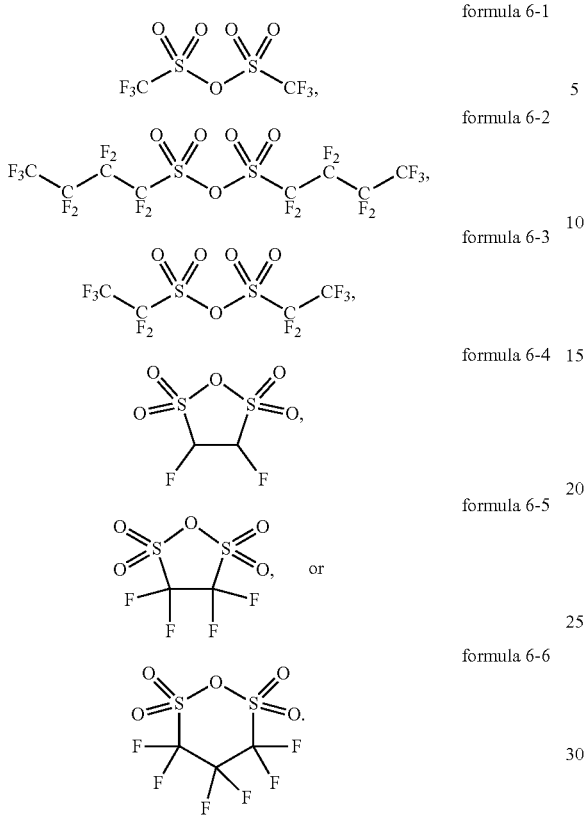

formula 6-1 formula 6-2 formula 6-3 formula 6-4 formula 6-5 formula 6-6

17. The electrochemical apparatus according to claim 8, wherein the positive active material comprises a lithium cobalt oxide, the lithium cobalt oxide comprises an element M, and the element M is one or more selected from the group consisting of Mg, Ti, Al, Zr, Sn, Zn, and Ca.

18. The electrochemical apparatus according to claim 17, wherein based on a total weight of the positive active material, the element M is 0.005 wt % to 1 wt %.

19. The electrochemical apparatus according to claim 8, wherein a specific surface area of the positive active material is 0.9 m²/g to 1.5 m²/g.

20. An electronic apparatus, comprising an electrochemical apparatus, wherein the electrochemical apparatus comprises:
a positive electrode, the positive electrode comprising a positive active material;
a negative electrode, the negative electrode comprising a negative active material; and
an electrolyte, comprising a compound of formula 1:

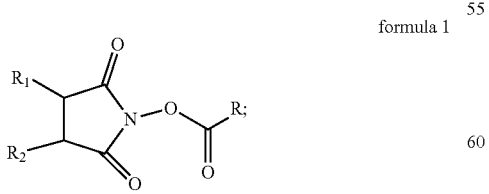

formula 1 wherein $R_1$ and $R_2$ are each independently selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group, a substituted or unsubstituted $C_{3-10}$ heteroaryl group, or any combination thereof;

wherein R is selected from a substituted or unsubstituted $C_{1-10}$ alkyl group, a substituted or unsubstituted $C_{3-10}$ cycloalkyl group, a substituted or unsubstituted $C_{2-10}$ alkenyl group, a substituted or unsubstituted $C_{2-10}$ alkynyl group, a substituted or unsubstituted $C_{1-10}$ alkoxy group, a substituted or unsubstituted $C_{6-10}$ aryl group or a substituted or unsubstituted $C_{3-10}$ heteroaryl group, a substituted or unsubstituted $C_{3-10}$ heterocycloalkyl group, a butyrolactam group,

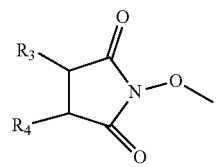

or any combination thereof;
wherein $R_3$ and $R_4$ are each independently selected from H, halogen atom, a substituted or unsubstituted $C_{1-3}$ alkyl group, a substituted or unsubstituted $C_{3-7}$ cycloalkyl group, a substituted or unsubstituted $C_{2-6}$ alkenyl group, a substituted or unsubstituted $C_{2-6}$ alkynyl group, a substituted or unsubstituted $C_{1-6}$ alkoxy group, or any combination thereof;

wherein when the substituent groups are each independently substituted, the substituent group is selected from at least one of halogen atom, a cyano group, a $C_{1-6}$ alkyl group, a $C_{3-6}$ cycloalkyl group, a $C_{1-6}$ alkoxy group, a $C_{2-6}$ alkenyl group, a $C_{6-10}$ aryl group, or a $C_{6-10}$ heteroaryl group; and wherein heteroatoms in the groups each are independently selected from at least one of O, S, N, or P;

wherein the electrolyte further comprises a nitrile compound; and the nitrile compound comprises a compound shown in formula 2, and at least one of a compound shown in formula 4 or a compound shown in formula 5:

NC—$R_{21}$—CN,  formula 2

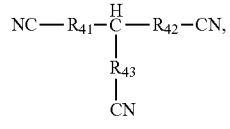  formula 4

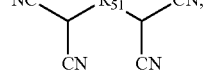  formula 5 wherein $R_{21}$ is selected from a substituted or unsubstituted $C_{1-5}$ alkylidene group or $R^c$—(O—$R^a$)$_A$—O—$R^b$, $R^a$ and $R^b$ are each independently selected from a substituted or unsubstituted $C_{1-3}$ alkylidene group, $R^c$ is selected from a single bonded or a substituted or unsubstituted $C_{1-3}$ alkylidene group, and A is an integer ranging from 0 to 2;

$R_{41}$, $R_{42}$ and $R_{43}$ are each independently selected from a single bonded or a substituted or unsubstituted $C_{1-5}$ alkylidene group, a substituted or unsubstituted $C_{1-5}$ alkyleneoxy group, or any combination thereof;

$R_{51}$ is selected from a substituted or unsubstituted $C_{1-5}$ alkylidene group, a substituted or unsubstituted $C_{3-7}$ cycloalkylidene group, a substituted or unsubstituted $C_{2-10}$ alkenylene group, a substituted or unsubstituted $C_{6-10}$ arylidene group, a substituted or unsubstituted $C_{1-6}$ heterocyclic group, or any combination thereof;

wherein when the substituent groups are each independently substituted, the substituent group is selected from at least one of halogen atom, a nitro group, a cyano group, a carboxyl group, and a sulfate group; and wherein based on a total weight of the electrolyte, the nitrile compound is 0.5 wt % to 10 wt %.

* * * * *